US011179551B2

(12) United States Patent
Nitzan et al.

(10) Patent No.: US 11,179,551 B2
(45) Date of Patent: *Nov. 23, 2021

(54) SYSTEM AND METHOD FOR TREATING PULMONARY EDEMA

(71) Applicant: White Swell Medical Ltd, Kibbutz Shefayim (IL)

(72) Inventors: Yaacov Nitzan, Hertzelia (IL); Menashe Yacoby, Ramat Gan (IL); Tanhum Feld, Merhavya (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/844,592

(22) Filed: Apr. 9, 2020

(65) Prior Publication Data

US 2020/0230380 A1 Jul. 23, 2020

Related U.S. Application Data

(63) Continuation of application No. 16/814,522, filed on Mar. 10, 2020, which is a continuation of application
(Continued)

(51) Int. Cl.
*A61M 27/00* (2006.01)
*A61M 1/36* (2006.01)
(Continued)

(52) U.S. Cl.
CPC ............ *A61M 27/002* (2013.01); *A61M 1/34* (2013.01); *A61M 1/3639* (2013.01);
(Continued)

(58) Field of Classification Search
CPC .... A61M 27/002; A61M 1/3689; A61M 1/34; A61M 1/3639; A61M 1/3653;
(Continued)

(56) References Cited

U.S. PATENT DOCUMENTS 3,211,150 A    10/1965   Foderick
3,926,175 A    12/1975   Allen et al.
(Continued)

FOREIGN PATENT DOCUMENTS

EP    0526102 A1    2/1993
EP    2353501 A1    8/2011
(Continued)

OTHER PUBLICATIONS

International Search Report and Written Opinion dated Apr. 12, 2018, for PCT/IB17/01488, filed Oct. 31, 2017 (11 pages).
(Continued)

*Primary Examiner* — Philip R Wiest
(74) *Attorney, Agent, or Firm* — Brown Rudnick LLP

(57) ABSTRACT

Systems, methods, and devices are provided for the treatment of edema. In one aspect a method for implanting an indwelling catheter within a vein of a patient is provided. The catheter can extend from a position upstream of at least one outflow port of a duct of the lymph system to a terminal position downstream of the at least one outflow port. In use, a first restriction can be created within the vein proximal to a distal region of the catheter. The first restriction can define a localized low pressure zone distal of the restriction and within a portion of the vein housing the catheter. The low pressure zone can be adjacent to the at least one outflow port to enable fluid to pass from the at least one lymph duct outflow port into the vein.

15 Claims, 21 Drawing Sheets

Related U.S. Application Data

No. 16/592,996, filed on Oct. 4, 2019, now Pat. No. 10,639,460, which is a continuation of application No. 16/225,453, filed on Dec. 19, 2018, now Pat. No. 10,709,878, which is a continuation of application No. 15/471,842, filed on Mar. 28, 2017, now Pat. No. 10,195,405, which is a continuation of application No. 14/625,930, filed on Feb. 19, 2015, now Pat. No. 9,901,722.

(60) Provisional application No. 62/006,206, filed on Jun. 1, 2014.

(51) Int. Cl.
  *A61M 1/34* (2006.01)
  *A61M 25/00* (2006.01)
  *A61M 25/10* (2013.01)

(52) U.S. Cl.
  CPC ........ *A61M 1/3653* (2013.01); *A61M 1/3655* (2013.01); *A61M 1/3659* (2014.02); *A61M 25/0026* (2013.01); *A61M 25/1011* (2013.01); *A61M 2025/0002* (2013.01); *A61M 2025/1015* (2013.01); *A61M 2025/1052* (2013.01); *A61M 2202/0405* (2013.01); *A61M 2205/10* (2013.01); *A61M 2205/3331* (2013.01); *A61M 2205/3334* (2013.01)

(58) Field of Classification Search
  CPC ............ A61M 1/3655; A61M 25/0026; A61M 25/1011; A61M 2025/0002; A61M 2025/1015; A61M 2202/0405; A61M 2205/10; A61M 2205/3331; A61M 2205/3334

See application file for complete search history.

(56) References Cited

U.S. PATENT DOCUMENTS

| | | |
|---|---|---|
| 4,714,460 A | 12/1987 | Calderon |
| 4,822,341 A | 4/1989 | Colone |
| 4,838,864 A | 6/1989 | Peterson |
| 4,957,484 A | 9/1990 | Murtfeldt |
| 5,005,564 A | 4/1991 | Grundei et al. |
| 5,069,662 A | 12/1991 | Bodden |
| 5,097,840 A | 3/1992 | Wallace et al. |
| 5,366,504 A | 11/1994 | Andersen et al. |
| 5,391,143 A | 2/1995 | Kensey |
| 5,484,412 A | 1/1996 | Pierpont |
| 5,509,897 A | 4/1996 | Twardowski et al. |
| 5,554,119 A | 9/1996 | Harrison et al. |
| 5,558,642 A | 9/1996 | Schweich, Jr. et al. |
| 5,716,340 A | 2/1998 | Schweich, Jr. et al. |
| 5,817,046 A | 10/1998 | Glickman |
| 5,836,912 A | 11/1998 | Kusleika |
| 5,893,841 A | 4/1999 | Glickman |
| 5,897,533 A | 4/1999 | Glickman |
| 5,908,407 A | 6/1999 | Frazee et al. |
| 5,919,163 A | 7/1999 | Glickman |
| 5,921,913 A | 7/1999 | Siess |
| 6,042,569 A | 3/2000 | Finch, Jr. et al. |
| 6,139,517 A | 10/2000 | Macoviak et al. |
| 6,152,945 A | 11/2000 | Bachinski et al. |
| 6,165,196 A | 12/2000 | Stack et al. |
| 6,179,796 B1 | 1/2001 | Waldridge |
| 6,183,492 B1 | 2/2001 | Hart et al. |
| 6,248,091 B1 | 6/2001 | Voelker |
| 6,254,563 B1 | 7/2001 | Macoviak et al. |
| 6,503,224 B1 | 1/2003 | Forman et al. |
| 6,524,323 B1 | 2/2003 | Nash et al. |
| 6,555,057 B1 | 4/2003 | Bendera |
| 6,616,623 B1 | 9/2003 | Kutushov |
| 6,635,068 B1 | 10/2003 | Dubrul et al. |
| 6,699,231 B1 | 3/2004 | Sterman et al. |
| 6,878,140 B2 | 4/2005 | Barbut |
| 6,936,057 B1 | 8/2005 | Nobles |
| 7,022,097 B2 | 4/2006 | Glickman |
| 7,195,608 B2 | 3/2007 | Burnett |
| 7,645,259 B2 | 1/2010 | Goldman |
| 7,766,892 B2 | 8/2010 | Keren et al. |
| 7,780,628 B1 | 8/2010 | Keren et al. |
| 8,109,880 B1 | 2/2012 | Pranevicius et al. |
| 8,126,538 B2 | 2/2012 | Shuros et al. |
| 8,216,122 B2 | 7/2012 | Kung |
| 8,480,555 B2 | 7/2013 | Kung |
| 8,679,057 B2 * | 3/2014 | Fulton, III ........ A61B 17/12045 604/96.01 |
| 9,179,921 B1 | 11/2015 | Morris |
| 9,405,942 B2 | 8/2016 | Liao et al. |
| 9,421,316 B2 | 8/2016 | Leeflang et al. |
| 9,433,713 B2 | 9/2016 | Corbett et al. |
| 9,486,566 B2 | 11/2016 | Siess |
| 9,533,054 B2 | 1/2017 | Yan et al. |
| 9,533,084 B2 | 1/2017 | Siess et al. |
| 9,642,991 B2 | 5/2017 | Eversull et al. |
| 9,669,142 B2 | 6/2017 | Spanier et al. |
| 9,669,144 B2 | 6/2017 | Spanier et al. |
| 9,675,739 B2 | 6/2017 | Tanner et al. |
| 9,682,223 B2 | 6/2017 | Callaghan et al. |
| 9,750,861 B2 | 9/2017 | Hastie et al. |
| 9,878,080 B2 | 1/2018 | Kaiser et al. |
| 9,901,722 B2 * | 2/2018 | Nitzan ............... A61M 25/1011 |
| 10,149,684 B2 | 12/2018 | Nitzan et al. |
| 10,154,846 B2 | 12/2018 | Nitzan et al. |
| 10,195,405 B2 | 2/2019 | Nitzan et al. |
| 10,207,086 B2 | 2/2019 | Nitzan et al. |
| 10,226,604 B2 | 3/2019 | Nitzan et al. |
| 10,226,605 B2 | 3/2019 | Nitzan et al. |
| 10,245,363 B1 | 4/2019 | Rowe |
| 10,285,708 B2 | 5/2019 | Nitzan et al. |
| 10,300,254 B2 | 5/2019 | Nitzan et al. |
| 10,653,871 B2 | 5/2020 | Nitzan et al. |
| 10,912,873 B2 | 2/2021 | Nitzan et al. |
| 10,926,069 B2 | 2/2021 | Nitzan et al. |
| 10,960,189 B2 | 3/2021 | Nitzan et al. |
| 2003/0093109 A1 | 5/2003 | Mauch |
| 2003/0134416 A1 | 7/2003 | Yamanishi et al. |
| 2004/0006306 A1 | 1/2004 | Evans et al. |
| 2004/0064091 A1 | 4/2004 | Keren et al. |
| 2004/0147871 A1 | 7/2004 | Burnett |
| 2004/0210296 A1 | 10/2004 | Schmitt et al. |
| 2004/0230181 A1 | 11/2004 | Cawood |
| 2005/0228474 A1 | 10/2005 | Laguna |
| 2005/0251180 A1 | 11/2005 | Burton et al. |
| 2006/0030814 A1 | 2/2006 | Valencia et al. |
| 2006/0064059 A1 | 3/2006 | Gelfand et al. |
| 2006/0100658 A1 | 5/2006 | Obana et al. |
| 2006/0178604 A1 | 8/2006 | Alderman |
| 2007/0055299 A1 | 3/2007 | Ishimaru et al. |
| 2007/0282303 A1 | 12/2007 | Nash et al. |
| 2007/0282382 A1 | 12/2007 | Shuros et al. |
| 2008/0009719 A1 | 1/2008 | Shuros et al. |
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0168649 A1 | 7/2010 | Schwartz et al. |
| 2010/0179389 A1 | 7/2010 | Moroney, III et al. |
| 2010/0280451 A1 | 11/2010 | Teeslink et al. |
| 2011/0004046 A1 | 1/2011 | Campbell et al. |
| 2011/0092955 A1 | 4/2011 | Purdy et al. |
| 2011/0257462 A1 | 10/2011 | Rodefeld et al. |
| 2011/0276023 A1 | 11/2011 | Leeflang et al. |
| 2011/0282274 A1 | 11/2011 | Fulton, III |
| 2011/0295302 A1 | 12/2011 | Mohl |
| 2012/0029466 A1 * | 2/2012 | Callaghan ........ A61M 39/0247 604/500 |

(56) References Cited

U.S. PATENT DOCUMENTS

| | | |
|---|---|---|
| 2012/0157913 A1 | 6/2012 | Aziz et al. |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0237954 A1 | 9/2013 | Shuros et al. |
| 2013/0245607 A1 | 9/2013 | Eversull et al. |
| 2013/0317535 A1 | 11/2013 | Demmy |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0169630 A1 | 6/2016 | Augustine et al. |
| 2016/0331378 A1 | 11/2016 | Nitzan et al. |
| 2017/0014563 A1 | 1/2017 | Khir |
| 2017/0095395 A1 | 4/2017 | Wennen et al. |
| 2017/0197021 A1 | 7/2017 | Nitzan et al. |
| 2017/0224512 A1 | 8/2017 | Hingston |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2019/0014991 A1 | 1/2019 | Maki et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0397963 A1 | 12/2020 | Nitzan et al. |
| 2021/0121678 A1 | 4/2021 | Nitzan et al. |

FOREIGN PATENT DOCUMENTS

| | | |
|---|---|---|
| EP | 2353503 A1 | 8/2011 |
| EP | 2637927 A1 | 9/2013 |
| WO | 89/04193 A1 | 5/1989 |
| WO | 01/013983 A2 | 3/2001 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2015/186003 A2 | 12/2015 |
| WO | 2017/087556 A1 | 5/2017 |
| WO | 2018172848 A2 | 9/2018 |

OTHER PUBLICATIONS

International Search Report and Written Opinion dated Jun. 25, 2018, for PCT/IB18/00263, filed Mar. 1, 2018 (10 pages).

International Search Report and Written Opinion dated Oct. 30, 2018, for PCT/IB18/000364, filed Mar. 19, 2018 (9 pages).

Non-Final Office Action issued in U.S. Appl. No. 15/799,562, dated Jul. 28, 2020 (8 pages).

Non-Final Office Action issued in U.S. Appl. No. 15/870,111, dated Jun. 24, 2020 (5 pages).

Bannon, 2011, Anatomic considerations for central venous cannulation, Risk Manag Healthc Policy 4:27-39.

Moscucci, 2014, Section III Hemodynamic principles 10 Pressure measurement, 223-244 in Grossman & Bairn's Cardiac Catheterization, Angiography, and Intervention 8 Ed.

Shimizu, 2014, Embolization of a fractured central venous catheter placed using the internal jugular apporach, Int J Surg Case Rep 5:219.

Stone, 2010, The effect of rigid cervical collars on internal jugular vein dimensions, Acad Emerg Med 17(1): 100-102.

Swan, 1970, Catheterization of the Heart in Man with Use of a Flow-directed Balloon-tipped Catheter, NEJM 283 (K9):447-451.

Yancy, 2013, 2013 ACCF/AHA Guideline for the Management of Heart Failure, Circulation 128(16):e240-e327.

\* cited by examiner

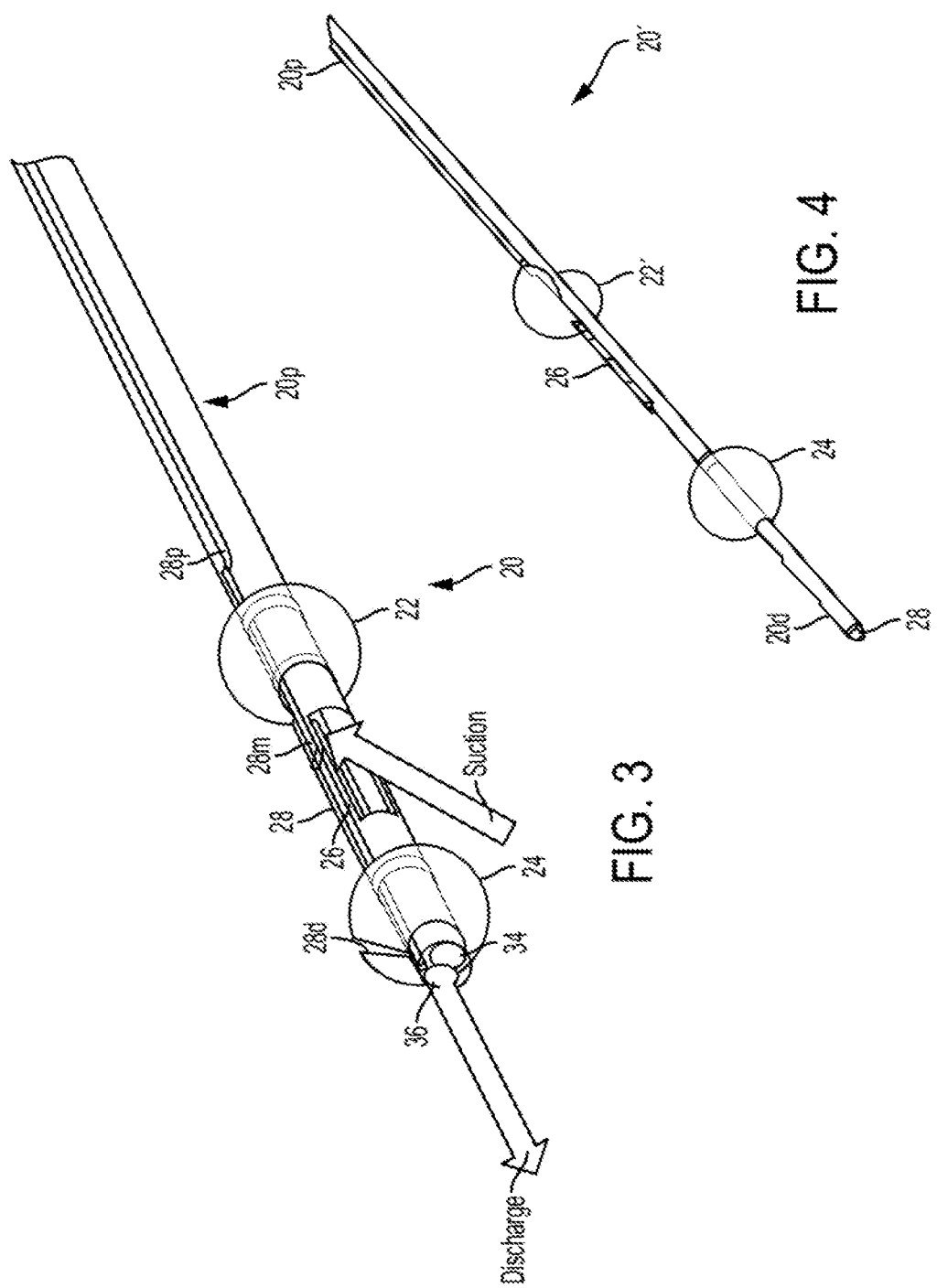

SYSTEM AND METHOD FOR TREATING PULMONARY EDEMA

CROSS REFERENCE

The present application is a continuation of U.S. patent application Ser. No. 16/814,522 filed on Mar. 10, 2020, which is a continuation of U.S. patent application Ser. No. 16/592,996 filed Oct. 4, 2019, which is a continuation of U.S. patent application Ser. No. 16/225,453 filed Dec. 19, 2018, which is a continuation of U.S. patent application Ser. No. 15/471,842 filed Mar. 28, 2017 (now U.S. Pat. No. 10,195,405), which is a continuation of U.S. patent application Ser. No. 14/625,930 filed Feb. 19, 2015 (now U.S. Pat. No. 9,901,722), which claims priority to U.S. Provisional Patent Application No. 62/006,206 filed Jun. 1, 2014, which are hereby incorporated by reference in their entireties.

FIELD

The present disclosure relates to surgical systems, devices and methods reducing pulmonary edema in a patient.

BACKGROUND

The lymphatic system is part of the circulatory system in conjunction with the arterial and venous systems. A primary function of the lymphatic system is to drain excessive interstitial fluid back into the venous system at two main locations: the thoracic duct and the lymphatic duct, which drain into the left and right subclavian veins, respectively.

Under normal circulatory conditions of the arterial and venous systems the interstitial fluid volume balance is maintained and the lymph fluid is cleared back through the lymphatic system. In pathological conditions such as Acute Cardiogenic Pulmonary Edema, the capillary hydrostatic pressure and the venous pulmonary pressure can become elevated and fluid flows excessively out of the blood vessels and into the interstitial and alveolar spaces. The pressure gradient between the initial lymphatics and at the outflow of the thoracic duct and the lymphatic duct is reduced and the lymphatic system cannot clear the additional fluid which accumulates in the air spaces of the lungs. This is a life threatening condition as gas exchange is impaired to the extent that it may lead to respiratory failure.

Current treatments methods require extended hospitalization and treatment with loop diuretics and or vasodilators. Oftentimes patients must also receive supplemental oxygen or, in more extreme cases, require mechanical ventilation. Many of these treatment methods are less than ideal because the edema is not always alleviated rapidly enough and for many patients renal function is adversely affected. A significant percentage of patients do not respond to this treatment and a significant percentage must be readmitted to a hospital within 30 days.

A significant problem with current treatment protocol is that it is based on the need to reduce intravascular blood pressure to move lymphatic fluid back into the vasculature. The reduction of intravascular blood pressure leads to leads to hypotension and activates the Renin Angiotenesin Aldesterone System, which leads to an increase in blood pressure. Eventually, this cycle leads to diuretic resistance and the worsening of renal function in almost 30% of admitted patients.

Accordingly, there remains a need for improved methods and devices for the rapid and effective removal of excessive fluid that accumulates as a result of pulmonary edema.

SUMMARY

Various methods and systems are provided for treating edema. In one aspect, the method includes implanting an indwelling catheter within a vein of a patient. The catheter can extend from a position upstream of at least one outflow port of a duct of the lymph system to a terminal position downstream of the at least one outflow port. A first restriction can be created within the vein proximal to a distal region of the catheter. The first restriction can define a localized low pressure zone distal of the restriction and within a portion of the vein housing the catheter. The localized low pressure zone can be adjacent to the at least one outflow port to enable fluid to pass from the at least one lymph duct outflow port into the vein. The first restriction can be a selectively expandable balloon formed on an outer wall of the catheter.

In another aspect, the method can include creating a second restriction within the vein that is distal to the first restriction and adjacent a distal portion of the catheter. In this aspect, the localized low pressure zone extends between the first and second restrictions. The second restriction can be a selectively expandable balloon formed on an outer wall of the catheter.

In another aspect, the catheter used with the method of treating edema is a multilumen catheter that includes a suction lumen and a discharge lumen. The suction lumen can be in communication with a suction port formed in the catheter to withdraw fluid from the vein through the action of an external pump. The discharge lumen can be in communication with a discharge line of the pump to return fluid to venous circulation through a discharge port in the catheter. In some aspects, the suction port can be disposed between the first and second restrictions and the discharge port can be disposed distal of the second restriction.

The catheter can be implanted in the internal jugular vein (right or left) and advanced to a position such that the discharge port is distal to the junction of the subclavian vein (right or left, depending on whether the catheter is implanted into the right of left internal jugular vein) and the internal jugular vein. The first restriction can be within the internal jugular vein (right or left). The second restriction can be within the innominate vein (right or left), and the suction port can be adjacent to the subclavian vein (right or left).

The catheter can include a plurality of control lumens, each configured to receive a pressure sensor. The pressure can be monitored in at least one position within the vein upstream of the first restriction, between the first and second restrictions, and downstream of the second restriction.

In other aspects, a second catheter can be implanted within a second vein. The second catheter can be in communication with an external pump. Fluid can be withdrawn from the second vein through the action of the pump and returned to the first catheter through a discharge line of the pump. In some aspects, the fluid can be discharged into the vein through a discharge port in the first catheter at a position downstream of the second restriction.

In some aspects, a hemofilter can be in communication with the discharge line of the pump. A diverter can be upstream of the hemofilter to direct some amount of the fluid withdrawn from the patient back to venous circulation while directing the remainder of the fluid to the hemofilter. After processing by the hemofilter, blood can be directed from the hemofilter back into venous circulation.

In another aspect, the system of treating edema, can include a catheter system configured for placement within a vein of a patient. The catheter system can have selectively deployable proximal and distal restrictions disposed within an indwelling portion of the catheter system. The catheter can include a blood inflow suction port disposed between the proximal and distal restrictions and in fluid communication with a suction lumen of the catheter system that is effective to remove fluid from venous circulation. A discharge port can be disposed distally of the distal restrictor and in fluid communication with a discharge lumen of the catheter and configured to return fluid to venous circulation. The system can include a pump configured to create a pressure differential to withdraw fluid from the suction port and through the suction lumen to withdraw a fluid within a vein from venous circulation and to return the fluid to venous circulation through the discharge lumen and the discharge port. A plurality of pressure sensors can be disposed within the catheter system. The pressure sensors can be configured to determine venous pressure upstream of the proximal restriction, between the proximal and distal restriction, and downstream of the distal restriction. The system also includes a control module that is to control operation of the system.

The pump can be configured to be positioned external to the patient, and in some aspects it can be a peristaltic flow pump.

In another aspect, an indwelling catheter configured to be implantable within a vein of a patient is provided. The catheter body can have a plurality of lumens, including a suction lumen configured to be in communication with a suction port of a pump and a discharge lumen configured to be in communication with a discharge line of the pump. The catheter can further include a plurality of sensor lumens, each configured to receive a pressure sensor, a selectively deployable proximal restriction disposed within a proximal region of the catheter body and a selectively deployable distal restriction disposed on at least a portion of an outer wall of the catheter body. The catheter can include a blood inflow suction port formed in a wall of the catheter and in fluid communication with the inflow lumen and a discharge port disposed distally of the second restriction. The catheter can include an inflation lumen for each of the first restriction and the second restriction.

The distal restriction can be a selectively inflatable balloon. In another embodiment, the proximal restriction is a selectively inflatable balloon. In some embodiments, the distance between the proximal and distal restrictions is in the range of about 1 to 15 cm. In some aspects, the suction port is disposed substantially midway between the proximal and distal restrictions.

In other embodiments, the indwelling catheter can have a diameter in the range of about 8 to 16 French. In some embodiments, each of the inflow lumen and the outflow lumen can have a diameter in the range of about 1 to 4 mm.

A sensor port can be in communication with each of the sensor lumens. In some aspects, a first sensor port can be disposed proximally of the proximal restriction, a second sensor port can be disposed between the proximal and distal restrictions, and a third sensor port can be disposed distally of the distal restriction.

In another aspect, a method of positioning an indwelling catheter for treating pulmonary edema is provided. The method includes inserting the indwelling catheter into a vein, such as the jugular vein of a patient. The indwelling catheter can be advanced until a distal restriction, a proximal sensor and a distal sensor positioned on the indwelling catheter are disposed within the jugular vein of the patient. The distal restriction can be activated until an initial pressure gradient is present between the proximal sensor and the distal sensor, which is disposed distally of the distal restriction. The distal restrictor activation level can be maintained at the activation level at which the pressure gradient is detected. The indwelling catheter can be advanced until the pressure gradient deviates from the initial pressure gradient between the proximal sensor and the distal sensor, thereby indicating a distal end of the indwelling catheter is positioned within a subclavian vein ostium of the patient. A percutaneous insertion length of the indwelling catheter can be observed. The indwelling catheter can then be advanced a pre-determined distance until the distal restrictor is within an innominate vein of the patient.

In yet another aspect, a system for treating edema includes a stent configured for placement within a vein of a patient. The stent has opposed ends with an expanded diameter configured to engage walls of a vein and a central portion having a reduced diameter. The stent further includes a fluid conduit extending therethrough from a first end to a second end and a suction conduit extending from a suction port formed in a central portion of the stent. The system also includes a pump configured to create a pressure differential to withdraw fluid from the suction port and through the suction conduit to withdraw a fluid adjacent to the suction port and the discharge port. A control module is also included in the system to control operation of the system.

BRIEF DESCRIPTION OF THE DRAWINGS

The invention will be more fully understood from the following detailed description taken in conjunction with the accompanying drawings, in which:

FIG. 3 is a detailed perspective view of a portion of the indwelling catheter as shown in FIG. 2;

FIG. 4 is a perspective view of a distal portion of an alternate embodiment of an indwelling catheter;

FIG. 14 is a graphical representation of the pressure gradient measured by the catheter as the catheter is advanced within a patient, approximately to a position shown in FIG. 11;

FIGS. 15-16 schematically illustrate and indwelling catheter being implanted within the venous system of a patient according to an alternate method of treading edema;

DETAILED DESCRIPTION

Figure 1:
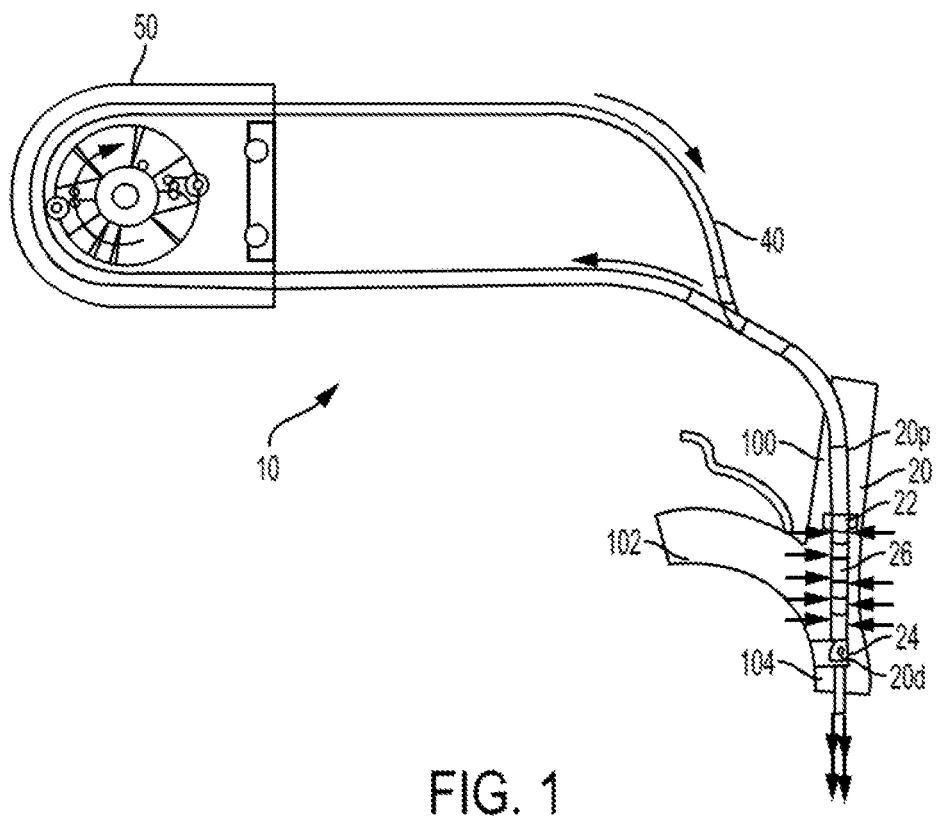
FIG. 1 is a schematic view of a system to treat pulmonary edema having an indwelling catheter and a pump.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for reducing edema conditions, such as pulmonary edema, in a patient by lowering the outflow pressure in a region around the thoracic/lymphatic duct outflow. As a result of lowering the outflow pressure at the thoracic and/or lymphatic ducts, higher lymphatic return will be achieved, enabling the lymphatic vessel flow to be at or near normal levels. In an exemplary embodiment, the systems and methods are particularly useful to treat acute pulmonary edema, however a person skilled in the art will appreciate that the systems and methods can be used in various procedures for treating a lymphatic system fluid clearance imbalance. In one embodiment, a catheter is provided for implantation within the vein of a patient in the vicinity of an outflow port of a duct of the lymphatic system. A first restriction can be created within the vein adjacent to a proximal region of the catheter and second restriction can be created within the vein adjacent to a distal region of the catheter. The first and the second restrictions define a localized low pressure zone within a portion of the vein housing the catheter. The low pressure zone can be adjacent to an outflow port to enable fluid to pass from the lymph duct outflow port to the vein.

A person skilled in the art will appreciate that the surgical systems, methods and devices disclosed herein can be used with a variety of surgical devices, including measuring devices, sensing devices, locator devices and insertion devices, etc.

The embodiments described herein generally relate to systems and methods for treating edema, including pulmonary edema. In some embodiments, the system can include any one or more of the following components: an indwelling catheter, a plurality of sensors, a control module, and a pump. The components of the system can rapidly alleviate the edema and increase the patient response rate.

FIG. 1 schematically illustrates one embodiment of a system 10 for treating pulmonary edema that includes an indwelling catheter 20 implanted within a vein of a patient and a pump 50, external to the patient, that is coupled to the catheter via drainage tubing 40. The pump and catheter system are positioned and cooperate so as to restrict blood flow within a vein, such as the jugular vein, so that the pressure in a localized region at the junction of the lymphatic vessel with the subclavian or jugular vein can be reduced. The indwelling catheter can have a proximal end 20p coupled to drainage tubing 40 that is in communication with the pump and a distal end 20d. As explained in detail below, the catheter 20 can be a multilumen catheter, with separate lumens to withdraw fluid from the vein to the pump 50 and to return fluid from the pump to the vein. Moreover, the catheter 20 can have a suction port 26 for withdrawing fluid from the vein into a suction lumen of the catheter for transport to the pump, and a discharge port 38, which can be at the distal end 20d of the catheter for the discharge of fluid back to the vein. The catheter 20 can also include pressure sensors and one or more selectively deployable restrictions (such as a first restriction 22, a second restriction 24) and the control lumens that communicate with the pressure sensors and restrictions.

The deployment of one or more of the restrictions, in combination with the rate at which fluid is removed from the vein, enables a pressure differential to be created in a localized region downstream of the first restriction 22 and adjacent to the junction of the jugular and subclavian veins, which is in the vicinity of the outflow ducts of the thoracic and/or lymphatic ducts. The pump 50 can be configured to remove fluid from the suction lumen of the catheter 20 (and thus the vein) through the pump and back through the catheter toward the distal end 20d for discharge back into the venous system at an appropriate rate to achieve the desired pressure differential. A control module configured, also discussed below, can be used to control the operation of the system.

Although, the system can be implanted with both proximal and distal restrictions, it can also be implanted with a single restriction as discussed below.

The systems and methods described herein have a number of advantages over existing techniques for treating pulmonary edema. In particular, a higher rate of fluid return from the thoracic and lymphatic outflow ducts enables faster lymphatic fluid removal and resolution of the edema episode. A risk of developing acute heart failure or compromised renal function may be avoided by rapid lymphatic fluid removal from the lymphatic system. As a result of this treatment method pressure in a relatively large area surrounding the thoracic and lymphatic ducts outflow ducts can be reduced thereby allow the procedure to be performed without complicated navigational guidance.

Figure 2:
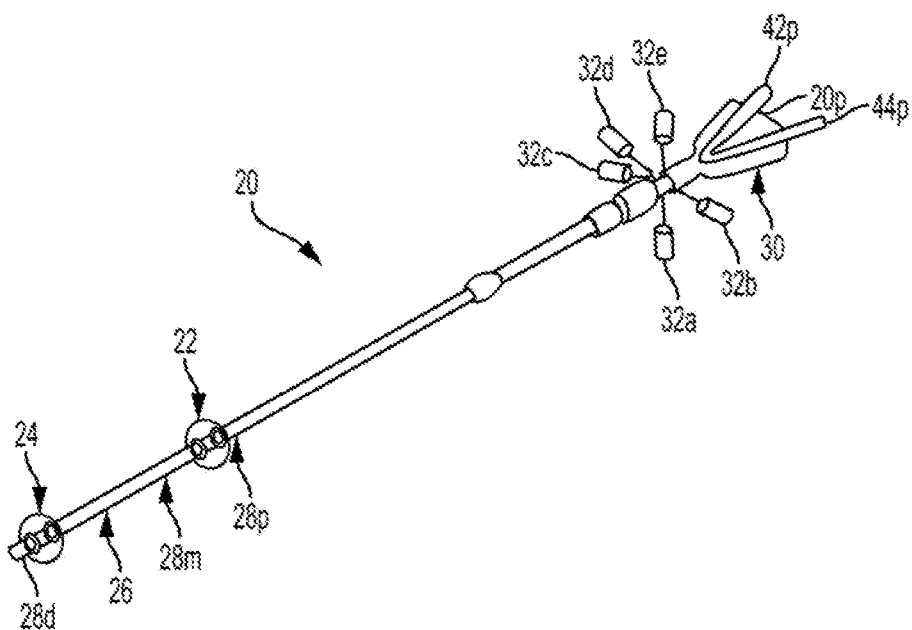
FIG. 2 a perspective view of an embodiment of an indwelling catheter.

A person skilled in the art will appreciate that a variety of indwelling catheter systems can be used to create the localized low pressure region described herein. FIGS. 2-4 illustrate an exemplary indwelling catheter 20 that can be used with the system described herein. The catheter 20 is configured such that at least a portion thereof is to be implanted within a vein of the patient, such as the internal jugular vein. As explained below, the catheter 20 is positioned such that a proximal portion that is implanted within the jugular vein is at a position that is upstream or proximal to the junction of the subclavian vein and a distal portion 20d is downstream or distal to this junction and may extend into the innominate vein.

It is understood that a variety of indwelling catheters can be used with the systems and methods described herein. By way of example, indwelling catheter 20 is a multilumen catheter having a generally elongate tubular shape, with a circular or ovular cross-sectional geometry as is known to those skilled in the art. The indwelling catheter 20 can include proximal end 20p, which is configured to be placed outside of a patient's body, and distal end 20d, which is configured for placement within a patient's vein.

Figure 5:
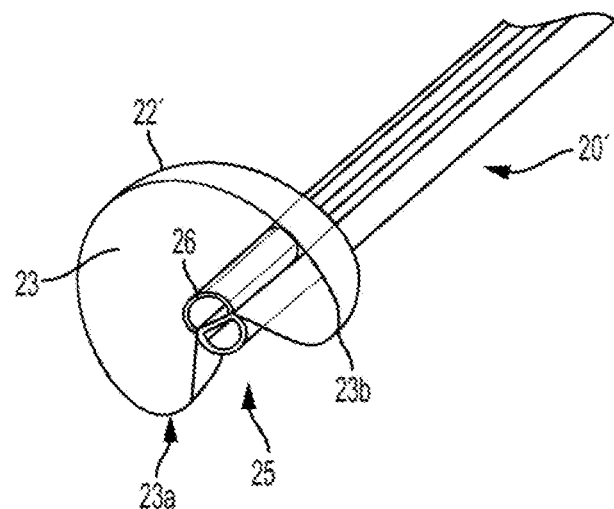
FIG. 5 is a cross sectional view of the indwelling catheter of FIG. 4 at line 5-5.

In one embodiment, the indwelling catheter 20 can include at least two lumens, including one to accommodate the flow of fluid from the vein in which the catheter is implanted to the pump 50, and one to accommodate the return of fluid from the pump to the vein. As shown in FIGS. 3 and 5, the catheter has a first lumen 34 and a second lumen 36 in a side-by-side relationship, both of which accommodate fluid flow between the vein and the pump 50. The first lumen 34 can be a suction lumen that extends from a suction port 26, formed in an outer wall 20o of catheter 20, to the proximal end of the catheter 20p. The proximal end 20p of the catheter 20 can include a hub 30 which communicates with discharge tubing 40 coupled to the pump 50 as shown in FIG. 1. Fluid is withdrawn from the vein through the suction port and into first (suction) lumen 34 so that it can be communicated to pump 50 via the discharge tubing 40. The second lumen 36 can be a discharge lumen that extends from the proximal end 20p of the catheter to discharge port 38 at the distal end 20d of the catheter 20. The discharge lumen 36 communicates via the hub 30 with the discharge tubing 40 of the pump 50 to return fluid from the pump 50 to venous circulation. To facilitate discharge and minimize retrograde backflow into the low pressure area the indwelling catheter can include a flared discharge port 38, as shown in FIG. 1. Although the first and second lumens 34, 36 are illustrated to be oriented in a side-by-side relationship with respect to one another, they can be oriented in any other suitable manner, including having one lumen disposed within the other lumen. As also discussed below, the catheter 20 can have a number of additional lumens, which function as control lumens to facilitate activation of restrictions within the catheter and/or to sense pressure at various locations within the vein in which the catheter is disposed.

As mentioned above and further shown in FIG. 2, the hub includes suction and discharge ports 42, 44, which can include surface features formed thereon and extending therearound to facilitate connection to discharge tubing 40. The inflow and outflow ports 42, 44 are configured to connect to drainage tubing having a first and a second end that is configured to be in fluid communication with the pump. The pump can facilitate fluid movement from the suction lumen through the outflow port 44 and into the discharge tubing through which it is communicated to the pump. The fluid can continue from the pump and into the drainage tubing through which it is communicated to the inflow port 42 and the discharge lumen within the indwelling catheter. Fluid is returned fluid back into venous circulation through the discharge lumen 36 so that it can be discharged at the distal end 20*d* of the indwelling catheter 20.

Figure 6:
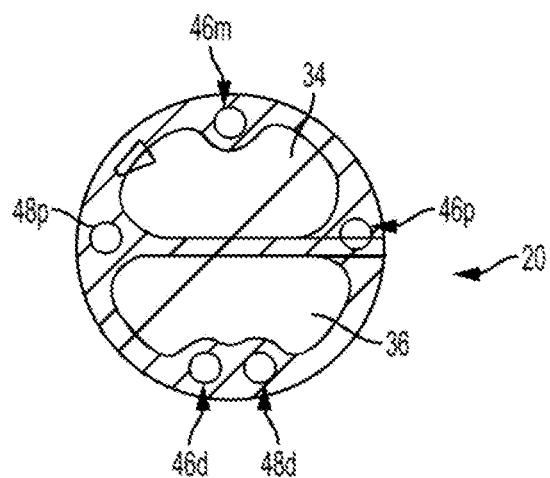
FIG. 6 is a cross sectional view of the indwelling catheter of FIG. 2 at line 6-6.

As shown in FIG. 2, the hub 30 also includes a number of ports 32*a*, 32*b*, 32*c*, 32*d* and 32*e* in fluid communication with control lumens within the catheter. As shown in FIGS. 2, 3, and 6, port 32*d* communicates with lumen 48*p*, which is configured to deliver fluid to restriction 22 to control the activation and deactivation of restriction 22. Similarly, port 32*a* communicates with lumen 48*d*, which is configured to deliver fluid to restriction 24 to control the activation and deactivation of restriction 24. Ports 32*b*, 32*e*, and 32*c* communicate, respectively, with control lumens 46*p*, 46*m*, and 46*d*. Control lumens 46*p*, 46*m*, and 46*d*, for example, can include pressure sensors to be used for sensing pressure at various locations along the vein in which the catheter is implanted. As shown in FIGS. 2-3 and 6, port 32*b* communicates with lumen 46*p*, which communicates with opening 28*p* in catheter 20 for purposes of sensing a pressure within the vessel in the vicinity of opening 28*p*, i.e., at a location proximal to restriction 22. Similarly, port 32*e* communicates with lumen 46*m*, which communicates with opening 28*m* in catheter 20 for purposes of sensing a pressure within the vessel in the vicinity of opening 28*m*, i.e., at a location distal to restriction 22 and in proximity to suction port 26. Also, port 32*c* communicates with lumen 46*d*, which communicates with opening 28*d* in catheter 20 for purposes of sensing a pressure within the vessel in the vicinity of opening 28*d*, i.e., at a location distal to restriction 24.

A person skilled in the art will appreciate that a variety of suitable sensors can be used for monitoring pressure.

As shown in FIG. 6, the catheter can be configured with the suction lumen 34 and the discharge lumen 36 oriented in a side-by-side arrangement. The control lumens 46*p*, 46*m*, 46*d*, 48*p*, and 48*d* can be disposed in the wall of the catheter 20. As indicated above, the cross sectional arrangement can have various embodiments. It is understood that the relative positioning of lumens 34 and 36 and control lumens 46*p*, 46*m*, 46*d*, 48*p*, and 48*d* can vary. A person skilled in the art will also appreciate that more or fewer lumens and control lumens can be provided in the catheter 20. For example, the control lumens can accommodate a variety of other sensors, such as heart rate sensors or breathing sensors which can be configured to be activation sensors.

A person skilled in the art will appreciate that the size of the catheter 20 can vary depending upon its intended uses. Generally, the catheter has a length in the range of about 15 to 50 cm. In addition, the diameter can also vary, but suitable catheters will typically be in the range of about 8 to 18 French. Similarly, the diameter of lumens 34 and 36 and control lumens 46*p*, 46*m*, 46*d*, 48*p*, and 48*d* can vary depending upon the requirements of a given application. Lumens 34 and 36 can have a diameter in the range of about 1 to 4 mm while control lumens 46*p*, 46*m*, 46*d*, 48*p*, and 48*d* can have a diameter in the range of about 0.1 to 0.5 mm.

As noted above, the indwelling catheter 20 includes at least one restriction to at least partially occlude the vein within which it is implanted and thus to restrict fluid flow within the vein when it is activated. A first restriction 22 is shown in FIGS. 2-5 as being positioned at a portion of the implanted catheter that is proximal to distal portion 20*d*. Typically, the first restriction 22 is positioned at a region of the catheter 20 that is proximal to suction port 26 and that will mark the proximal or upstream boundary of the reduced pressure region. By way of example, in a catheter implanted within the jugular vein, as shown in FIG. 1, the first restriction is proximal to (upstream of) the point at which the subclavian vein enters the jugular vein. The indwelling catheter can optionally include a second restriction 24 positioned distally of the first restriction 22 and between the suction port 26 and the distal end 20*d* of the catheter 20. By way of example, and as shown in FIGS. 1-3, in a catheter implanted within the jugular vein, the second restriction 24 is distal to the point at which the subclavian vein enters the jugular vein, and it can be in the innominate vein.

Although the system can be used with proximal and distal restrictions, it can also be implemented with a single proximal restriction.

A person skilled in the art will appreciate that the restrictions can take a variety of forms as long as they are effective to at least partially occlude the vessel within which they are deployed. The proximal restriction 22 should be configured so as to partially restrict flow when it is activated, but to allow some fluid to flow past the restriction. The distal restriction 24, on the other hand, can be configured to fully restrict fluid flow when it is activated. The purpose of the restrictors is to allow the normal flow of blood to continue. However, the activation of the restrictions creates a localized pressure differential between the region proximal to the proximal restriction and the region between the two restrictions.

In some embodiments, as shown in FIGS. 2 and 3, the first and second restrictions 22, 24 can be in the form of a symmetrical inflatable member, such as a balloon, that will expand in a uniform manner around a center axis of each restriction. The proximal restriction can be configured and/ or activated such that when fully activated or inflated, the restriction will not occupy the entire diameter of the vein within which it is positioned. A person skilled in the art will appreciate that the restriction (e.g., a balloon) can be configured in a number of ways so as not to occupy the entire diameter of the vein in which it is deployed. For example, and as described below, the restriction can be configured to expand asymmetrically, such as by having part of the outer wall of the restriction attached to the outer wall of the catheter so that uniform expansion of the restriction is prevented. Typically, in the expanded condition the first restriction 22 will occupy about 50 to 90 percent of the diameter of the vein within which it is implanted. The distal restriction 24 can be similarly configured if it is to permit some fluid flow and not fully occlude the vein. On the other hand, the distal restriction 24 can be configured to fully occupy the diameter of the vein when it is activated.

FIG. 4 illustrates one example of a catheter 20' that is similar in construction to catheter 20, described above, except that proximal restriction 22' is configured to expand asymmetrically to ensure only partial occlusion of the vein within which it is implanted. Catheter 20' includes a suction port 26 and a discharge port 28, which is adjacent to distal portion 20*d*. Restriction 22' is disposed proximal to suction port 26 and, as noted above, it is configured to expand asymmetrically while distal restriction 24 expands symmetrically. As shown in FIGS. 4 and 5, restriction 22' can be of a non-circular shape in its expanded condition such that it does not circumscribe the entire circumference of catheter 20'. In one example, restriction 22' can be substantially kidney-shaped with a body portion 23 that serves to occlude the vein in which it is implanted and a gap in the body portion that is positioned between body edges 23*a*, 23*b*. The restriction 22' can be configured to occlude approximately 50 to 95 percent of the diameter of the vessel within which it is positioned. A person skilled in the art will appreciate that restriction 22' can be assembled to the catheter in a number of ways to enable the formation of a kidney-like shape upon expansion that serves to partially occlude a vessel. For example, FIG. 5 shows that the catheter 20' can have the restriction 22' extending from only a portion of the circumference of the catheter 20', for example from only about half of the catheter. The catheter can further include a distal tip 28d' that includes a discharge port that can facilitate fluid transport from the catheter back into the venous system.

A person skilled in the art will appreciate that the restrictions 22, 22', and 24 can be in the form of a balloon of the type typically used in interventional medical devices, such as a compliant or semi-compliant balloon. Accordingly, the restrictions can be made of a variety of materials that expand upon the delivery of a fluid thereto and contract upon the withdrawal of such fluid. Exemplary materials from which the restrictions can be made include polymeric materials such as PEBAX, silicones, polyurethanes, and nylons.

Figure 7A:
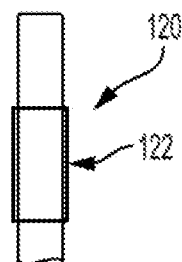
FIG. 7A is a side perspective view of a portion of an indwelling catheter of the type shown in FIG. 2 having a restriction in a deflated configuration.
Figure 7B:
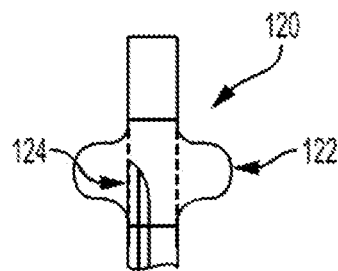
FIG. 7B is a side perspective view of a portion of an indwelling catheter of the type shown in FIG. 7A having a restriction in an inflated configuration.

As noted above, the restrictions can be activated and deactivated during the treatment procedure. For example, FIGS. 7A and 7B illustrate a restriction 122 in the form of a balloon or a double balloon. The restriction 122 can be formed around all or a part of the outer wall of the catheter, and it can be in fluid communication with a control lumen such as an inflation lumen. When a fluid is communicated to the restriction 122 to effect inflation, the control lumen can remain at the initial fixed diameter while the restriction expands. FIG. 7A illustrates the restriction 122 in an inactivated or deflated state in which it is contracted and surrounding an outer wall of the catheter 120. FIG. 7B illustrates the inflation lumen 124 and restriction 122 in an expanded or inflated form.

Figure 7C:
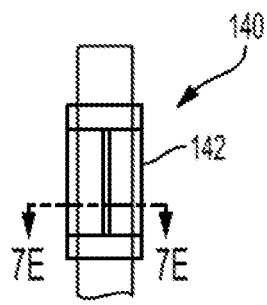
FIG. 7C is a side perspective view of a portion of another embodiment of an indwelling catheter having an alternate restriction in a deflated configuration.
Figure 7D:
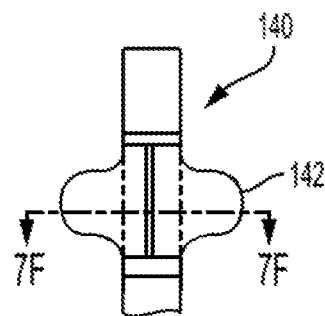
FIG. 7D is a side perspective view of a portion of another embodiment of an indwelling catheter of the type shown in FIG. 7C having an alternate restriction in an expanded configuration.
Figure 7E:
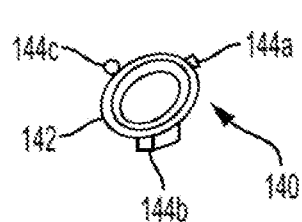
FIG. 7E is a cross sectional view at line 7E-7E of the indwelling catheter shown in FIG. 7C with the restriction in a deflated configuration.
Figure 7F:
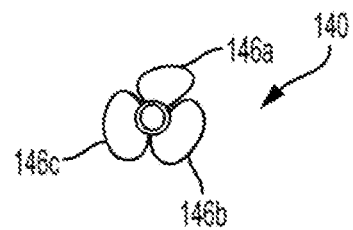
FIG. 7F is a cross sectional view at line 7F-7F of the indwelling catheter shown in FIG. 7D with the restriction in an expanded configuration.

In some embodiments, alternate geometries can be used for the restrictions to prevent the restriction from fully occluding a vein or to prevent the vein lumen from fully collapsing on the indwelling catheter. For example, FIGS. 7C-7F illustrate another embodiment of a restriction positioned on an indwelling catheter 140. FIG. 7C illustrates an alternate restriction 142 in an inactivated or deflated state and FIG. 7E is a cross sectional view of the catheter 140 of FIG. 7C. As shown, the restriction 142 can be in the form of three balloon segments 146a, 146b, 146c that can be positioned around the outer circumference of the catheter 140 and that are separated by three restriction nodes 144a, 144b, 144c that constrict the balloon segments 146a, 146b, and 146c. FIG. 7D is a perspective view of the indwelling catheter 140 in an expanded position, while FIG. 7F illustrates a cross sectional view of the indwelling catheter 140 with the three restriction nodes 144a, 144b, 144c constricting the balloon segments 146a, 146b, and 146c when the balloon segments are in expanded state. The restriction nodes 144a, 144b, 144c can be fully or partially engaged and can be expanded uniformly or to varying positions based on the particular constraints of the anatomy of the patient. The constraints positioned around the circumference of the restriction can prevent the restriction from expanding in a circular geometry. Restriction of the circular geometry can ensure that blood can flow past the restriction at all times and is a safety mechanism against the vein collapsing on the restriction and restricting blood from flowing past the first or the second restriction. A person skilled in the art will appreciate that the formation of balloon segments can be achieved by the use of an external restrictive structure, such as rigid cup with three openings which is mounted external to the balloon. Alternatively, the balloon segments can be formed by bonding the balloon inner wall to the catheter shaft along three longitudinal lines. Alternatively, the balloon can be bonded to the shaft along circumferential segment. Such a segment will not be free to inflate and thus only the free, non-bonded segment will be inflated, resulting in an asymmetric cross section of the balloon.

Figure 7G:
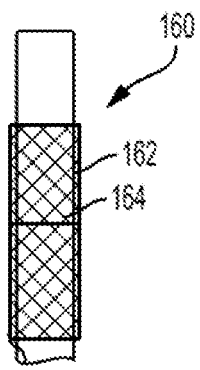
FIG. 7G is a side perspective view of a portion of an indwelling catheter having a retaining frame and a restriction in a deflated configuration.
Figure 7H:
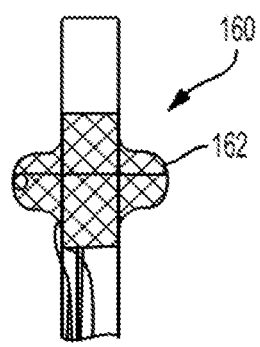
FIG. 7H is a side perspective view of a portion of the indwelling catheter as shown in FIG. 7G having the restriction in an inflated configuration.

In some embodiments, as shown in FIGS. 7G-7H, a covered frame or an activation wire comprising a braided wire or the like can be used to constrict or modify the geometry of the restrictions. For example, FIG. 7G illustrates a perspective view of an indwelling catheter 160 with a restriction 162 in an initial or an unexpanded state. The restriction 162 is surrounded by a braided wire 164. Upon activation, as shown in FIG. 7H, the restriction 162 can expand but, the covered frame 164 limits the expansion to prevent the restriction 162 from expanding into a full circular geometry.

Figure 8:
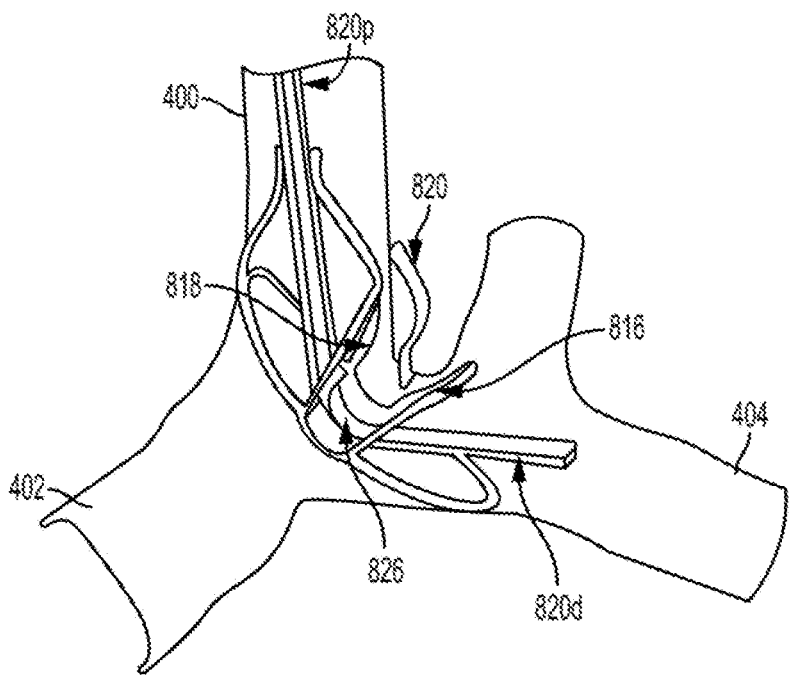
FIG. 8 is a schematic view of an alternate embodiment of an indwelling catheter and frame in a deployed configuration.
Figure 8A:
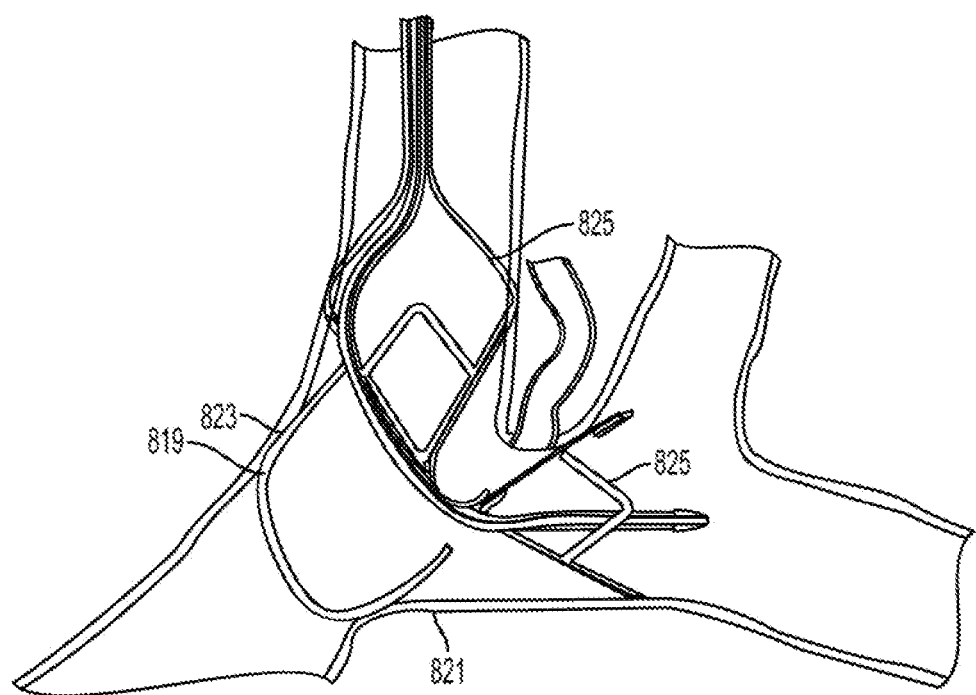
FIG. 8A is a further schematic view of the indwelling catheter and frame of FIG. 8 in a deployed configuration.

Other restriction designs are possible as well. In some embodiments, a frame can be used to isolate the area proximate to the outflow duct. As shown in FIG. 8, this embodiment can utilize a catheter 820 coupled to a Nitinol frame 816. The catheter can be configured to a L-shape upon activation of the Nitinol frame, with a guiding distal end 820d, a rounded midsection 820m having a suction port 826, and a proximal section 820p having a discharge port. The catheter 820 can be proximate to or coupled directly to the frame. The frame 816 can be formed of a shape memory material that can be crimped during insertion to about 14 Fr or less and can be introduced to the bifurcation of the jugular vein. The crimped section of the frame can expand from an initial position wrapped or closely aligned with the catheter to a u-shaped geometry as shown in FIG. 8, upon deployment within the left or right sides of the subclavian 402 or internal jugular veins 400. The frame 816 can include a membrane 818, stretched across the frame to partition a low pressure zone proximate to the thoracic duct. As shown in FIG. 8A, the frame can have an additional segment 819 that will support either the innominate vein 821 wall or both the innominate vein wall and the subclavian vein wall 823 to ensure contact of the membrane edge with the venous wall to enable pressure reduction of the isolated area. Also, the frame segments within the subclavian and jugular vessel can have multiple struts 825 that will ensure a patent section for blood flow. The membrane can be formed from polymeric materials such as polyurethane, silicones, polyethylene terephthalate (PET), and polyethylene tetrafluoroethylene (PTFE). Additionally, materials having varying levels of porosity can also be used. Exemplary materials with varying levels of porosity include expandable polyethylene tetrafluoroethylene (ePTFE), PET fabric, and polyester fabric.

The catheter can be inserted into a vein such as the jugular vein (on either the right or left side of the patient's body) and advanced to a position in the vicinity of a bifurcation in the vein and advanced to position the portion of the frame having the membrane proximate to the thoracic duct. After insertion of the catheter, the frame can be deployed from the crimped position to the expanded position, forming an angled configuration segmenting a portion of the vein from the surrounding area. Thereafter, the area proximate to the thoracic duct is isolated and fluid can be removed via a suction port positioned on the catheter located within the isolated area. Fluid can then be discharged through the discharge port on the catheter back into the venous system within the jugular vein 400. As explained below, the pumping of fluid can be performed by a rotating impeller within the catheter between the suction and discharge ports, or by an external pump such as peristaltic pump that will pump the fluid from the isolated area through suction lumen outside the patient and then return the fluid through the discharge lumen to the blood stream outside of the isolated area. A pressure sensing lumen, which is positioned proximately to the catheter suction port within the isolated area, can be used to control the rate of suction by maintaining the pressure of the isolated area between about 2-5 mmHg and thus prevent collapse of the thoracic duct due to excessive suction and ensure optimized lymph drainage. The patent area behind the membrane enables blood flow from the subclavian and jugular vein without interruption.

For all active platforms for regulating lymphatic flow including pumps, mechanical activation, electrical activation and neural activation the system may include sensors that may help optimize the lymphatic regulation. In addition to the placement of such sensors in the indwelling catheter, the sensors can be placed at various positions that may be prone to the accumulation of interstitial fluid. For example, blood pressure sensors can be placed in the venous system, in the heart, in the arterial system, at the junction of the subclavian and jugular veins, and in the body at other target sites. Additionally, another type of sensor, such as a fluid sensor, can be used to measure the amount of fluid in the body, specifically in the interstitial spaces of the lungs. The sensors can detect a rise in the fluid or the pressure of the lung cavity and actuate the pump to enable higher flow volumes to enhance the lymphatic clearance. Such sensors may further include bioimpedance sensors, radio frequency transmitters and receivers, and optical means that measure changes in the body organ dimensions. Additional sensors may include heart rate sensors, breathing sensors and activity sensors.

In the event that a patient develops edema, an acute treatment option involves implanting within the patient's venous system, such as the internal jugular vein, an indwelling catheter of the type discussed above. The catheter can be coupled through fluid return tubing via an external pump 50 to connect the suction lumen of the catheter to the discharge lumen via drainage tubing. The pump 50 can be operated to create a localized low pressure region at the junction of the jugular, subclavian and innominate veins to establish a pressure gradient in the vicinity of the thoracic and lymphatic duct outflow.

A person skilled in the art will appreciate that a variety of pumps can be used as part of the system 10 described herein. Examples of suitable pumps include peristaltic pumps, impeller pumps, and piston pumps. In some embodiments, a peristaltic pump can be used to withdraw fluid through the indwelling catheter to reduce pressures surrounding the thoracic and lymphatic duct outflow thereby assisting in removing excess lymphatic fluid from the thoracic and/or the lymphatic duct. Suitable pumps, for example, should be capable of operating at a flow rate in the range of about 100 ml/min to 800 ml/min and typically in the range of about 400 ml/min to 800 ml/min. Pump operation in the range of about 400 ml/min to 800 ml/min can reduce the pressure in the vicinity of the thoracic and lymphatic duct outflow by more than about 50%. For example, the optimal outflow pressure of the thoracic and lymphatic duct outflow is approximately 5 mmHg, and pressures in excess of 25 mmHg can completely stop lymphatic return. The pump can be operated to reduce high pressures at the thoracic and lymphatic duct outflow to an optimally low pressure in the range of about 2 mmHg to 6 mmHg in—less than about twenty-four hours. Exemplary pumps include the Watson Marlow 520R2 peristaltic pump head with 0.64 mm bore and 2.4 mm wall silicon tubing pump.

The low pressure region corresponds to the drainage ports of the thoracic and lymphatic ducts and can enable enhanced clearance of lymphatic fluids. For example, the pressure between the first restriction and the second restriction will be reduced often from about 10 mmHg-20 mmHg to about 2 mmHg-6 mmHg. The pressure at the distal end of the catheter proximate to the discharge port can be mildly elevated but by no more than 2 mmHg.

Figure 9A:
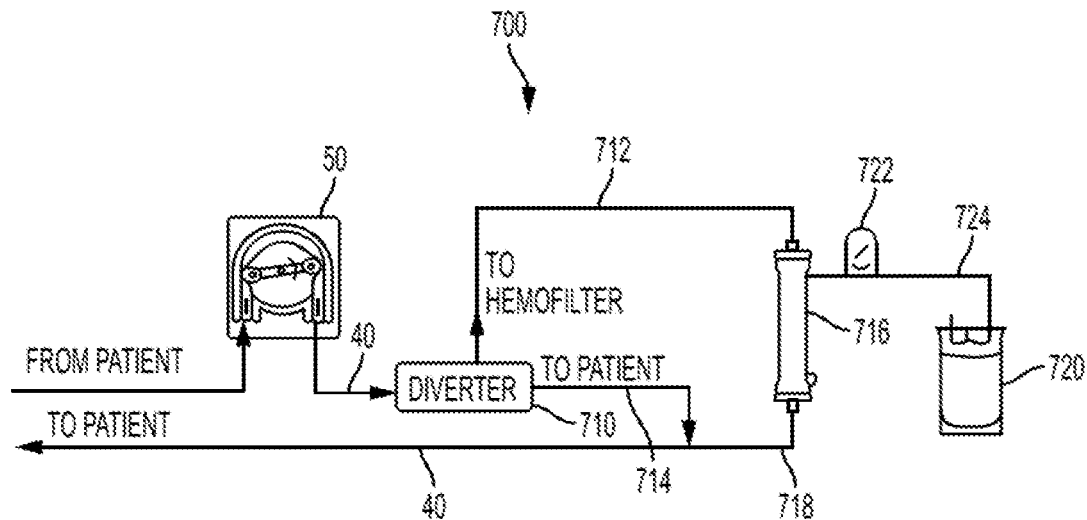
FIG. 9A is a schematic view of an alternate embodiment of a system to treat pulmonary edema including a hemofilter and a diverter.

In some embodiments, ultrafiltration can be used to reduce acutely decompensated heart failure via removal of fluids outside of the body. Ultrafiltration process, which can utilize a hemofilter as described below, can be useful to remove additional fluid volume that was added to the blood through the lymphatic system so as to not rely solely on the kidneys to remove excess fluid. As shown in FIG. 9A a hemofilter circuit 700 can be incorporated into the system 10. After fluid exits pump 50 through discharge tubing 40, it passes through a diverter 710. Diverter 710 diverts a certain volume of fluid, generally equal to the amount of lymphatic fluid drained from the body (e.g., up to about 10 ml/min) and diverts it to hemofilter through line 712. The remaining volume of fluid is allowed to flow into a downstream section of discharge tubing 40 through line 714. Such a diverter can be in the form of "Y" connector. As the accumulated pressure drop along lines 712, 714, and 718 (filter line) equals the pressure drop along 714 line, proper selection of the inner diameter and length of line 714 can help achieve the desired blood flow rate through the hemofilter 716. In one example, a filter is suitable to work with blood flow rate of about 100-500 ml/min, where the total blood flow through the system is about 600 ml/min. At a blood flow rate of about 200 cc/min the filter can be expected to have a pressure drop of about 30 mmHg. In this example, the line 714 segment is 25 cm in length with 2.5 mm inner diameter. At a blood flow of 400 cc/min through line 714, the pressure drop is 30 mmHg and thus matches the pressure drop along the filter line. As shown in FIG. 9A, line 712 passes the excess fluid to a hemofilter 716 where the blood is separated from the lymphatic fluid. Blood is passed from hemofilter 716 back into downstream discharge tubing 40 through line 718. As shown in FIG. 9A, lymphatic fluid can be discharged from hemofilter 716 into a collection chamber 720. A roller pump 722 may be placed in discharge line 724 to continuously regulate the volume of withdrawn lymphatic fluid. Alternatively, a clamp or tap may be placed in the discharge line 724 and regulation of withdrawn lymphatic fluid can be achieved be opening and closing the clamp or tap.

The use of a hemofilter can be advantageous to reduce the blood volume in the cardiovascular system, thereby reducing the pressure and allowing fluids to flow from the interstitial spaces back into the venous system and relieve the edema. However, the reduced blood volume can adversely impact kidney function. The use of ultrafiltration as described herein can reduce the pressure and fluid volume in a localized area where the lymphatic system drains into the venous circulation. The overall system volume is not reduced and thereby limits the adverse impact on the kidney function of a patient. In some embodiments, a controllable amount of the fluid is circulated through a pump and diverted to a filter. Typically it will be around 10 to 40 percent of the volume but it could be manipulated by a flow restrictor on a Y connector that diverts some of the flow into a filter. The filter can be configured to control the blood volume thereby preventing a change due to the lymphatic drainage.

Figure 9B:
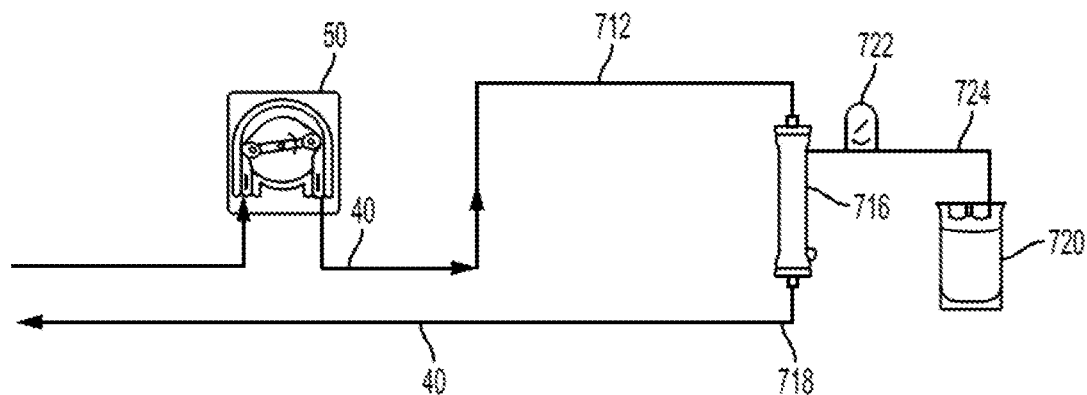
FIG. 9B is a schematic view of an alternate embodiment of a system to treat pulmonary edema including a hemofilter.

In another embodiment, as shown in FIG. 9B, the hemofilter circuit 700 can be incorporated into the system 10. After fluid exits pump 50 through discharge tubing 40, it passes the excess fluid to the hemofilter 716 where the blood is separated from the lymphatic fluid. Blood is passed from hemofilter 716 back into downstream discharge tubing 40 through line 718. As shown in FIG. 8B, lymphatic fluid can be discharged from hemofilter 716 into the collection chamber 720. A roller pump 722 may be placed in discharge line 724 to control the volume of withdrawn lymphatic fluid.

A person skilled in the art will appreciate that a variety of hemofilters can be used as part of the system 700 described herein. Suitable hemofilters, for example, should be capable of operating at a flow rate in the range of about 10 ml/min. Exemplary hemofilters include the Sorin Hemocor HPH mini and the Sorin Hemocor HPH Junior.

Figure 10:
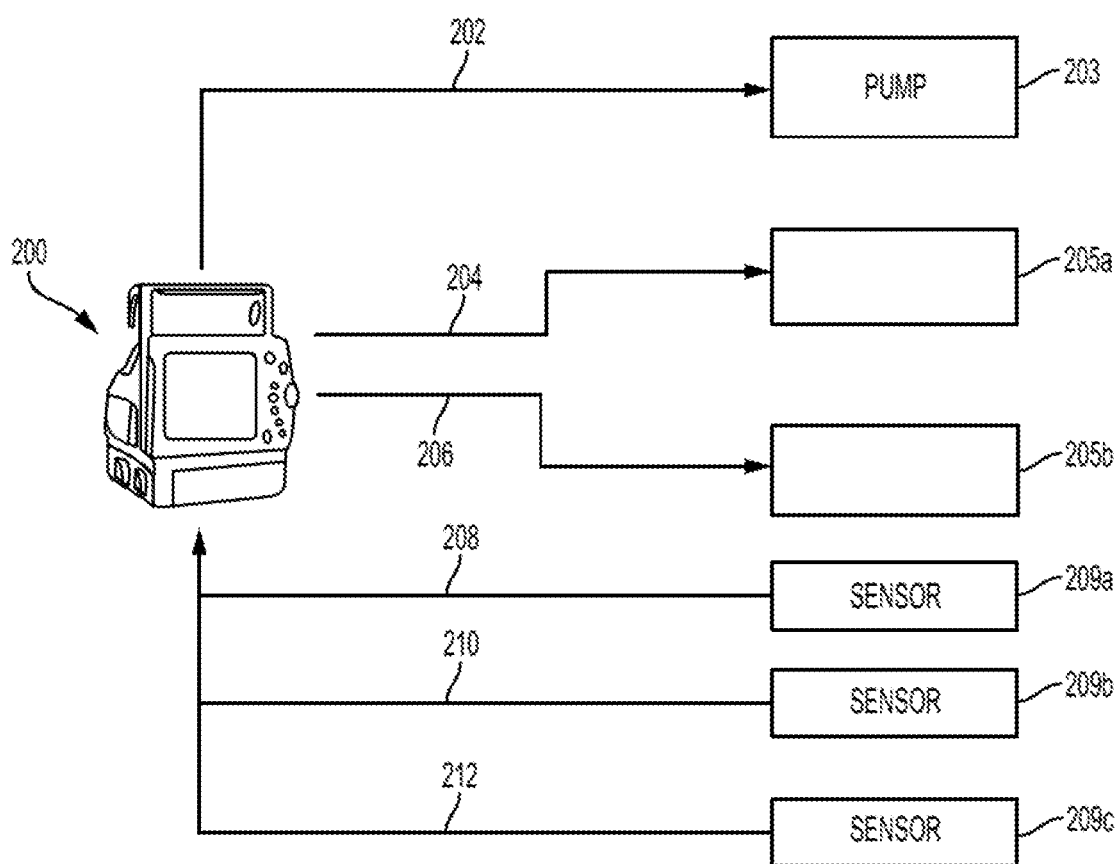
FIG. 10 is a block diagram schematically illustrating operation of a control module for a system for treating edema.

The system to treat pulmonary edema can further include a control module to receive information from the sensors, activate the restrictions, and adjust the flow rate of the pump. In some embodiments, as shown in FIG. 10, the system to treat pulmonary edema can include a control module 200 configured to receive information from pressure transducers 209a, 209b, 209c including information regarding the pressure 208 within the jugular vein, the pressure 210 at the bifurcation of the jugular and subclavian veins, and the pressure 212 at the innominate vein. Upon receiving the data from the various pressure transducers the control module can be configured to actuate the pump function of pump 203. The control module 200 can further be configured to process the data received from the various sensors to alter the first or second restriction volume 204, 206 via an automated, and travel controlled syringe pump 205a, 205b.

Figure 11A:
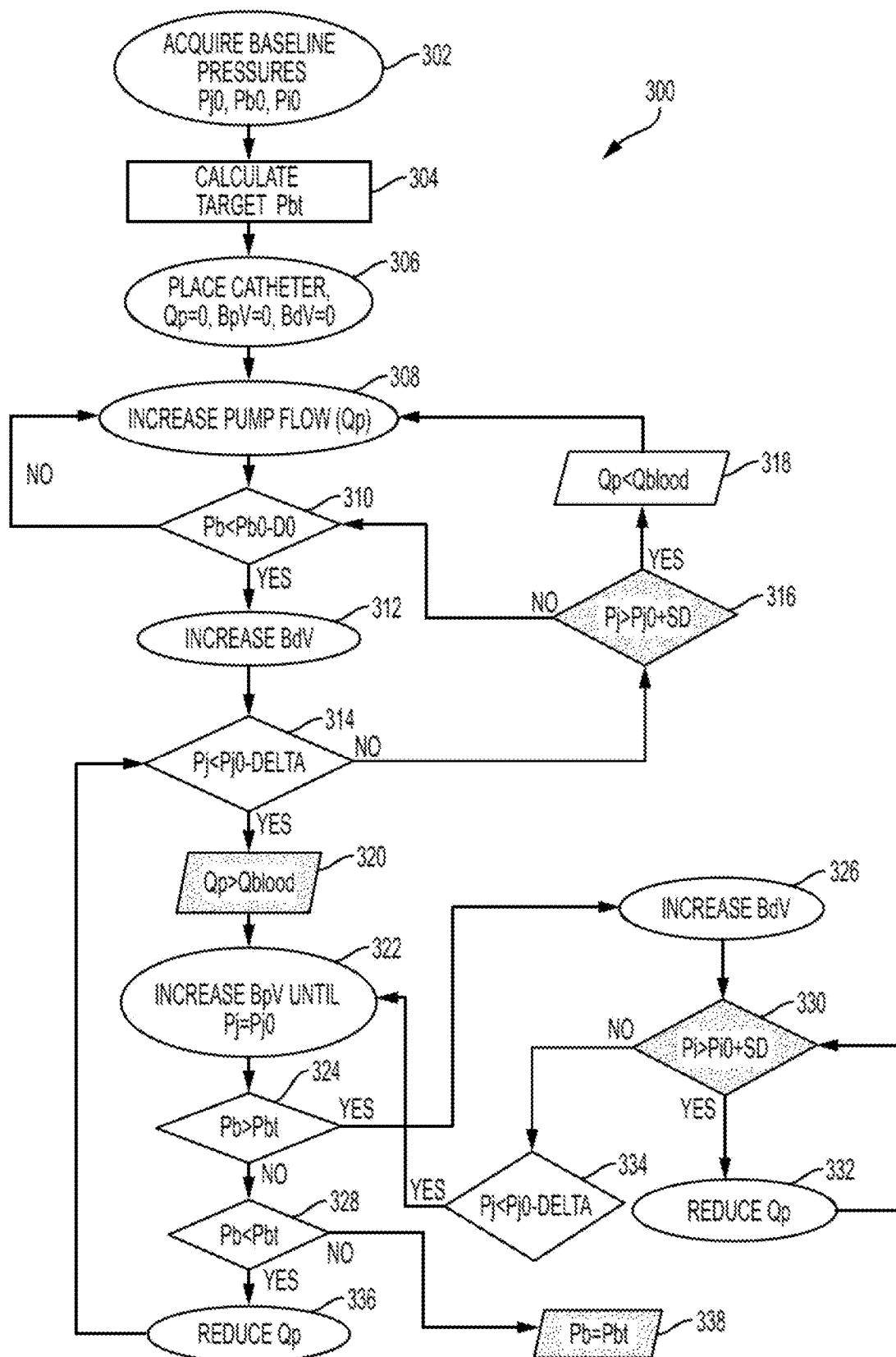
FIG. 11A is a flow diagram for operation of a control module for a system for treating edema.

The control module 200 can include multiple feedback loops to adjust performance of the system 10 to create and maintain a low pressure zone while the lymphatic fluid is cleared. In some embodiments, as shown in FIG. 11A, A system to treat edema can include a control module 200 configured to execute a process 300 to create a low pressure zone and transport fluid from the low pressure zone back into the venous system of a patient. For example, at step 302 the control module can acquire the baseline measurement for the jugular pressure, the bifurcation pressure and the innominate pressure. The control module at step 304 can then calculate the target bifurcation pressure to a value typically in the range of about 3-5 mmHg. At step 306 the catheter can be placed and the pump flow rate can equal zero, and the volume of the first and the second restrictions that can also be equal to zero. Next, at step 308 the control module increases the pump flow rate. At step 310 the control module determines if the baseline pressure is less than the baseline bifurcation pressure minus the pressure drop indicator. If this proves to be the case, the control process advances to step 312 and increases the volume of the second restriction. If the pressure baseline is greater than the baseline bifurcation pressure minus the pressure drop indicator then the process returns to step 308 and the pump flow rate is thereby increased.

After the second restriction volume is increased, at step 314 the data from the jugular vein pressure is analyzed to determine if the jugular vein pressure is less than the baseline jugular pressure minus the minimum significant pressure deviation. If the jugular vein pressure is greater than the baseline jugular pressure minus the minimum significant pressure deviation process continues to step 316. At step 316, an algorithm analyzes if the jugular pressure is greater than the baseline jugular pressure plus the safety delta. If yes, the process continues to step 318, and the pump flow rate is less than the natural blood flow rate into the innominate vein. The process continues back to step 308 and the pump flow rate is increased.

At step 316, if the jugular pressure is less than the baseline jugular pressure plus the safety delta then the process continues to step 310, where, as discussed above, step 310 determines if the bifurcation pressure is less than the baseline bifurcation pressure minus the pressure drop indicator. At step 310 the process either continues on to step 312 or reverts back to step 308 as discussed above.

At step 314, if the jugular pressure is less than the baseline jugular pressure minus the minimum significant pressure deviation then the process continues on to process step 320, where the pump flow rate is greater than the natural blood flow rate into the innominate vein. The process then advances to step 322 where the first restriction inflation volume is increased until the jugular pressure is greater than the baseline jugular pressure. The process advances to step 324 where the control module determines if the bifurcation pressure is greater than the target bifurcation pressure. The value of the target bifurcation pressure is typically in the range of about 3-5 mmHg. If the target bifurcation pressure is greater than the baseline pressure then the process advances to step 328. If the bifurcation pressure is equal to the target bifurcation pressure then the process stops at step 338. In such cases where the bifurcation pressure is unstable and exceeds the target bifurcation pressure, the process advances to step 336 to reduce the pump flow volume and the process returns to step 314 and repeats as described above.

Alternatively, if at step 324, the bifurcation pressure is greater than the target bifurcation pressure then the process advances to step 326, where the second restriction inflation volume is increased. The process then advances to step 300, where the algorithm determines if the innominate pressure is greater than the baseline innominate pressure plus the safety delta. If yes, the process advances to step 332 where the pump flow rate is reduces and the process repeats step 330. If the innominate pressure is greater than the baseline innominate pressure plus the safety delta, then the process reaches step 334 and reverts to process step 322 and advances as described above.

Figure 11B:
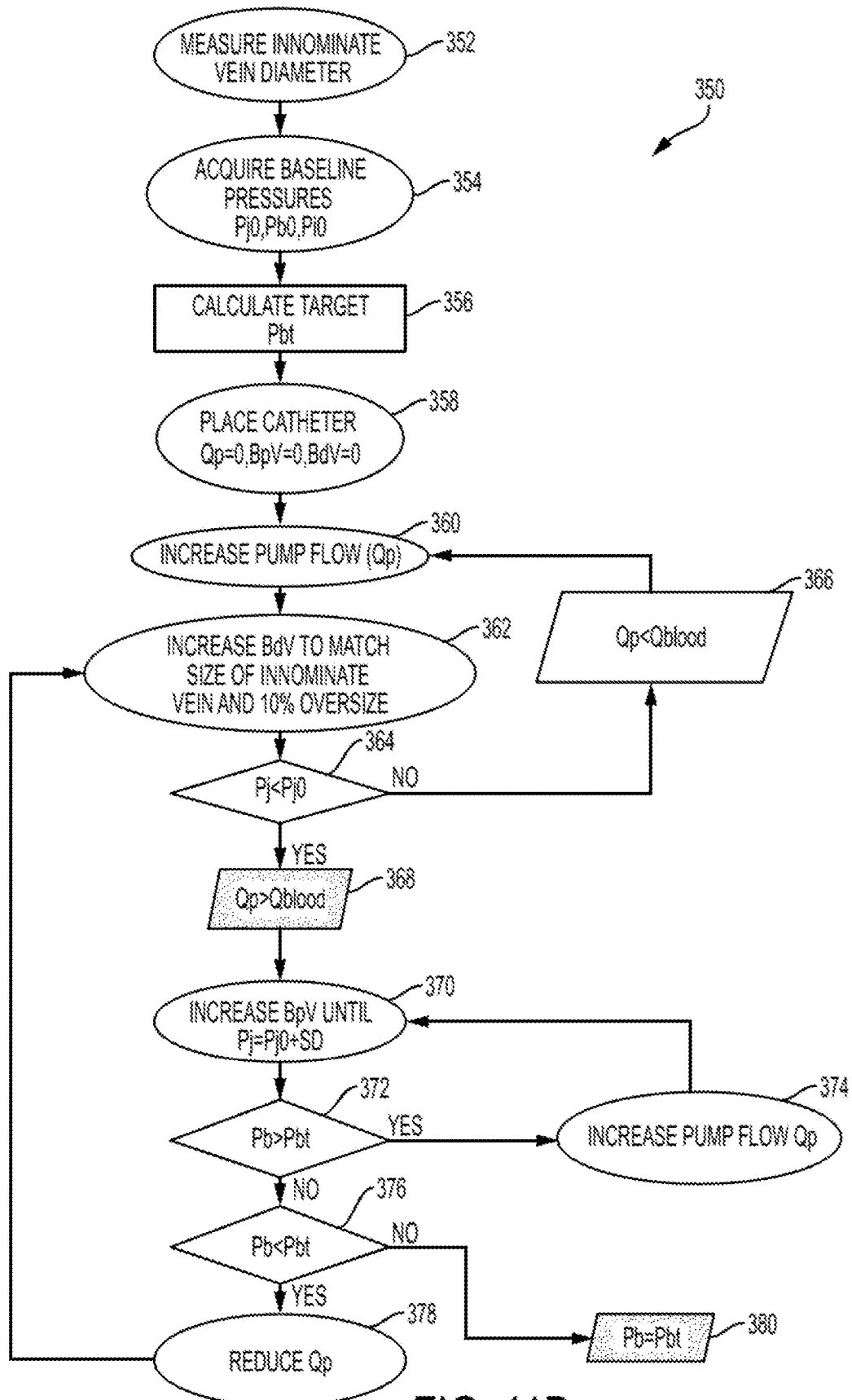
FIG. 11B is a flow diagram for an alternative technique for placing a catheter within a patient according to a method of treating edema.

FIG. 11B illustrates an alternative technique for placing a catheter including process 350, which can be useful when there is preexisting knowledge of a patient's anatomy, for example as a result of data provided by fluoroscopy or another imaging technique that includes the innominate vein diameter. According to this technique, the distal balloon is inflated to a known diameter, for example to about 10 percent greater than the nominal innominate vein diameter. For example, at step 352, the diameter of the innominate vein can be acquired by the control module. The control module can measure baseline data for the jugular pressure, the bifurcation pressure and the innominate pressure at step 354. At step 356, the target bifurcation pressure can be calculated by the control module, typically, in the range of about 3-5 mmHg. At step 358, the catheter can be placed. During placement of the catheter, the pump flow rate, the proximal balloon inflation volume and the distal balloon inflation volume are typically equal to about zero.

After the catheter is placed in the venous system, the pump flow rate can be increased at step 360. After the pump flow rate is increased, at step 362, the proximal balloon inflation volume can be increased to match the size of the innominate vein. In some embodiments, the inflation volume can be up to ten percent oversized. At step 364, the control module applies an algorithm to analyze if the jugular pressure is less than the baseline jugular pressure. If not, at step 366, an algorithm is applied to confirm that the pump flow rate is less than the normal blood flow rate into the innominate vein. The process then continues to step 360, where, as discussed above the pump flow rate can be increased.

At step 364, if the jugular pressure is less than the baseline jugular pressure then, the process continues to step 368. At step 368, the control module applies an algorithm to analyze whether the pump flow rate is greater than the natural blood flow rate into the innominate vein. Thereafter, at step 370, the proximal balloon inflation volume can be increased until the jugular pressure is equal to the baseline jugular pressure plus a safety delta. The safety delta can typically be in the range of about 2-3 mmHg. At step 372, the control module applies an algorithm to measure the bifurcation pressure. If the bifurcation pressure is greater than the target bifurcation pressure, then the process can proceed to step 374, and the pump flow rate can be increased. The process then can continue back to step 370 where, as discussed above, the proximal balloon inflation volume can be measured.

If at step 372, the bifurcation pressure is less than the target bifurcation pressure, the process continues to step 376. At step 376, the control module applies an algorithm to confirm that the bifurcation pressure is less than the target bifurcation pressure. If yes, the process continues to step 378 where the pump flow rate can be decreased and the process returns back to step 364. At step 364, the algorithm can measure jugular pressure and the process continues as described above. At step 376, if the algorithm confirms that the bifurcation pressure is equal to the target bifurcation pressure the process continues to step 380 and the process terminates.

As mentioned above, an acute treatment for edema, as described herein, involves inserting an indwelling catheter into a vein of a patient. In some embodiments, the method can include placing an indwelling catheter at an internal jugular vein (left or right) with a central line procedure, according to techniques well known to those skilled in the art. It is understood that the catheter can alternately be inserted into open veins such as the subclavian, external jugular or auxiliary veins. The placement technique is well known to those skilled in the art and it can typically be conducted using a 12 Fr sheath to puncture the venous wall. The distal restriction, when activated, isolates the incoming blood flow from the subclavian and jugular veins from the blood flow of the innominate vein and ensures that all incoming blood is directed to the pump. The pump is activated to maintain the jugular and innominate vein pressure and thus the nominal blood flow. The proximal restriction, when activated, creates a pressure gradient between the upper jugular vein and the subclavian vein. As the nominal pressure of the jugular vein is maintained by the actuation of the pump, the pressure gradient across the proximal restriction is achieved by the pressure reduction within the area between the two restrictions. Actuation of the pump helps to create a low pressure zone in the vicinity of the junction of the jugular vein and the subclavian vein by withdrawing fluid in this region, recirculating it through the pump, and discharging the fluid downstream of this region. Because the outflow of the thoracic and lymphatic ducts is located in this region, the lower pressure will facilitate drainage of lymphatic fluid.

Figure 12:
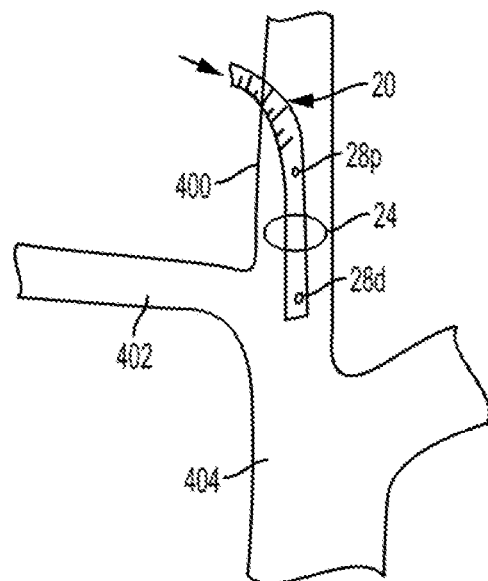
FIGS. 12-15 schematically illustrate an indwelling catheter being implanted within the venous system of a patient according to a method of treating edema.
Figure 13:
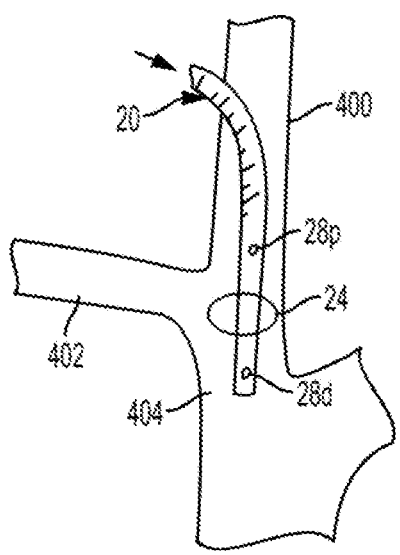
Figure 14:
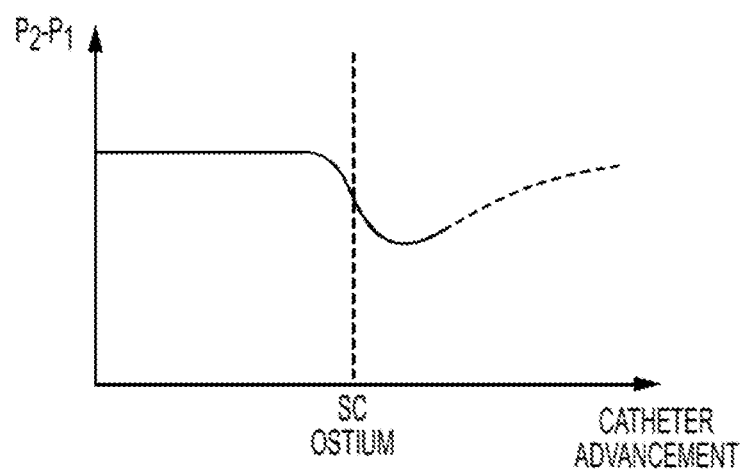

FIGS. 12-14 illustrate methods for implanting an indwelling catheter within the vein of a patient. As shown in FIG. 10, the indwelling catheter 20 can be inserted into the right internal jugular vein 400 of a patient. The indwelling catheter 20 can then be advanced until the distal restriction 24 and the distal pressure sensing opening 28d, are within the jugular vein 400. The distal restriction 24 is activated while the proximal pressure sensing opening 28p and the distal pressure sensing opening 28d measure the venous pressure both distal and proximal to the distal restriction 24. When a pressure gradient is achieved, typically about 2-5 mmHg, inflation of the distal restriction 24 can be terminated. The indwelling catheter 20 can then be advanced further into the internal jugular vein 400, while the inflation of the restriction 24 is maintained and the pressure is monitored at the proximal pressure sensing opening 28p and the distal pressure sensing opening 28d. As shown in FIG. 14, when the proximal pressure sensing lumen and the distal pressure sensing lumen indicate a drop in the pressure gradient, the distal restriction has moved past the subclavian vein and into the subclavian vein ostium. The indwelling catheter 20 can include indicia that can be used to ascertain the distance that the catheter has traveled within the vein of the patient. After the pressure drop is detected, as shown in FIG. 13, the indwelling catheter 20 can be advanced an additional 1-2 cm distally thereby moving the distal restriction into the innominate vein 404.

In another embodiment, a catheter with a single restriction (e.g., balloon) can be used. The catheter can also include two pressure sensing control lumens, with one sensing pressure proximal to the restriction and the other sensing pressure distal to the balloon. The catheter can be used by positioning the restriction within the innominate vein and to fully inflate it to the vessel diameter. The flow rate applied to the pump will be greater than the natural rate of flow within the patient's vascular system. This higher flow rate of the pump will help to create low pressure zone within the patient just proximal to the restriction.

Figure 15:
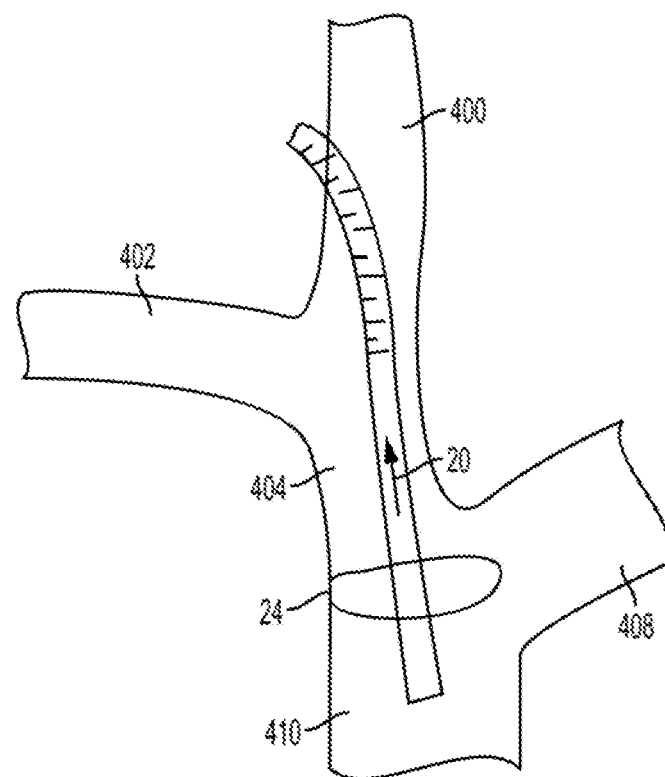
Figure 16:
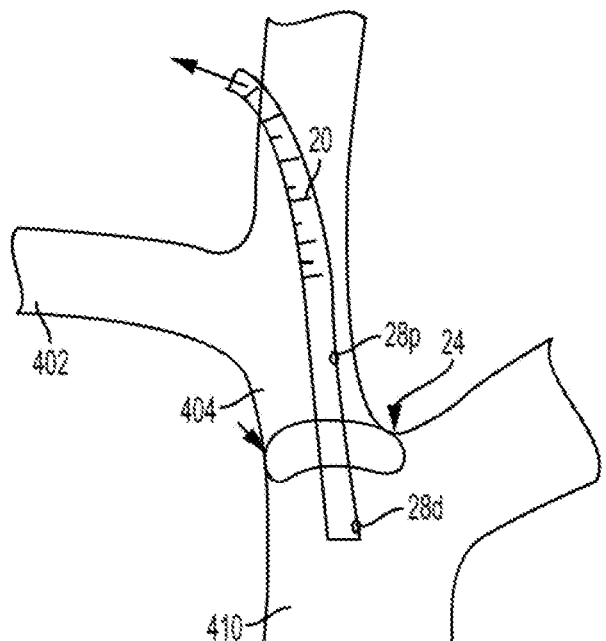
Figure 17:
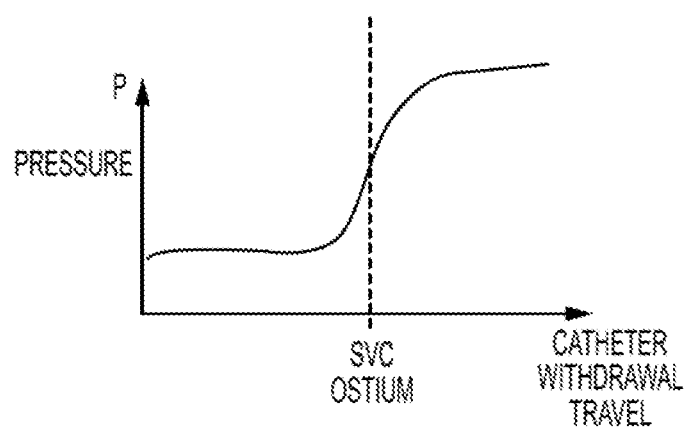
FIG. 17 is a graphical representation of the pressure gradient measured by the catheter as the catheter is withdrawn within a patient, approximately to a position shown in FIG. 13.

In some embodiments, as shown in FIGS. 15-17, an alternate catheter insertion technique can be used and catheter positioning can be achieved without the use of imaging modalities. As explained below, only the distal restriction is utilized for purposes of catheter positioning and only after the catheter is properly positioned is the system activated. By way of example, as shown in FIG. 15, the indwelling catheter is introduced into the jugular vein 400 of the patient. The indwelling catheter 20 is advanced approximately 15 cm thereby positioning the distal end 20d within the superior vena cava (SVC) 410 while the distal pressure sensing opening 28d monitors the pressure. As shown in FIG. 14, the distal restriction 24 is activated while the proximal pressure sensing opening 28p and the distal pressure sensing opening 28d monitor the pressure. Once the pressure gradient is in the range of about 2-5 mmHg, the distal restriction 24 is maintained at its current activation level. After activation of the distal restriction 24, retrograde movement of the indwelling catheter 20 can begin while also monitoring the pressure gradient proximal to the distal restriction 24. As shown in FIG. 17, when the proximal pressure sensing opening 28p indicates an elevated proximal pressure, the distal restriction 24 is in a position adjacent to the innominate vein ostium 408. As discussed above, the catheter indicia can be used to indicate the insertion distance and or position within a patient. The distal restriction 24 can then be deactivated while moving the catheter retrograde by a distance of about 1-2 mm, the distal restriction is now placed within the innominate vein 404.

After positioning the indwelling catheter within the vein of a patient by a technique as discussed above, the indwelling catheter will have the suction port 26 positioned proximate to an outflow port of a duct of the lymphatic system.

The indwelling catheter's sensors can be used to attain a baseline pressure measurement in the internal jugular, SVC and the junction of the jugular and subclavian veins. After establishing a pressure baseline, the restrictions can be deployed and the pump can be activated.

In some embodiments the pump can initially operate at a rate of about 200 ml/min. In conjunction with the pump operation, the first and second restrictions 22, 24 can be activated and deactivated to adjust the pressure and thereby create a localized low pressure zone within a portion of the vein housing the indwelling catheter 20. The pump 50 can continue to increase the pump rate at increments of about 100 ml/min while the pressure is continuously monitored. The first and second restrictions 24, 26 can be adjusted to alter the innominate vein and the SVC pressures from the baseline. Once the localized low pressure zone has been created, thereby reducing the pressure to about 50% its baseline value, or the pump has reached 800 ml/min, the system parameters are held constant while the pump 50 continues to operate.

Alternate Catheter Embodiments

In some embodiments, alternate catheter designs can be used in place of the indwelling catheters discussed above. As discussed below, these alternative catheters include, catheters with an alternate lumen configurations, catheters with a single lumen and a one way valve, catheters with a propeller operation, catheters having a piston operation, self-stabilizing catheters, and split action catheters.

In one embodiment, an alternate catheter can include a coaxial lumen configuration. For example, in an alternate lumen configuration an inner lumen can be positioned within an outer lumen. The outer lumen can have perforations in the outer wall of the catheter that can be configured to act as the suction ports to extract fluid from the low pressure area. The inner lumen can be configured to be isolated from the outer lumen and can function as the discharge lumen. The coaxial lumen catheter can be used in the system as described above to create a low pressure area proximate to the lymphatic duct thereby removing fluid from the low pressure area and returning the fluid to the venous system via the peristaltic pump.

Figure 21:
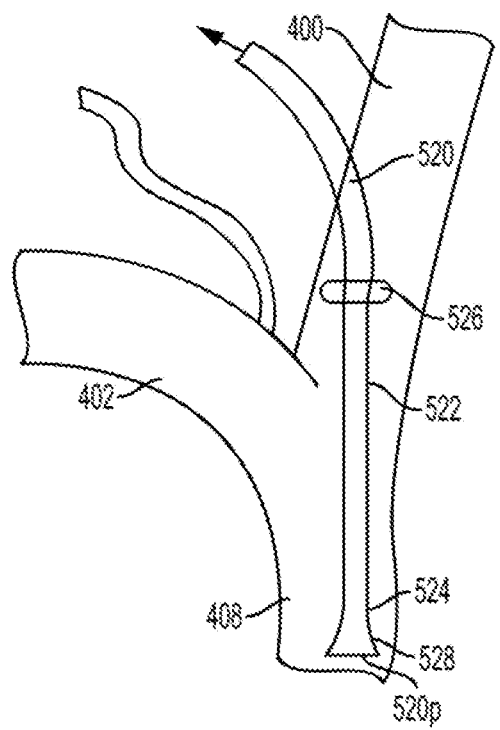
FIG. 21 is a schematic view of a single lumen catheter having two one way valves inserted within a patient.
Figure 22:
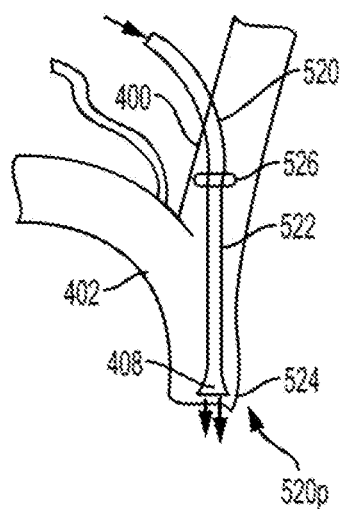
FIG. 22 is a schematic view of the catheter as shown in FIG. 20 further depicting fluid flow from the distal end of the catheter.

In another alternate embodiment, as shown in FIGS. 21 and 22, a catheter can have a single lumen 520 configured with two one-way valves, with one positioned at the proximal restriction and one at the distal end of the catheter. As shown in FIGS. 21 and 22, the pressure reduction via suction and discharge can be performed in a pulsatile pattern. For example, when suction is performed in the single lumen catheter 520 a first one way valve 524 will disable entry of blood from the discharge port into the catheter. Fluid is drawn towards the proximal end of the catheter thereby creating a low pressure area proximate to the lymphatic duct. Fluid can be drained from the lymphatic duct into the low pressure area. Alternately, when discharge is performed fluid will move from the proximal end of the catheter toward the distal end. A second one way valve 522 will disable the discharge of fluids back into the suction port and will ensure that the fluids are transported into the discharge port 520*p* and back into the venous system.

In another embodiment, a catheter can include a self-stabilizing mechanism. For example, in some embodiments catheters can be configured to expand to a larger diameter once inserted within the vein of a patient. For example, a catheter can be inserted via a puncture site into the vein system having a diameter of about 6 Fr and expand to about 15 Fr each immediately when inserted inside the vein. Such expansion of a catheter can reduce the need for high velocity and turbulence of fluid flow. The only location where there will be a small diameter inside the 12. Fr sheath that will assist in the crossing of the system through the venous wall in the puncture site. The flaring and crimping of the catheters can also be enabled upon retracting the system back through the sheath. The expansion and contraction of the system can eliminate the need for a supplemental stability system as the embodiment can self-stabilize via its internal structural integrity.

Figure 23:
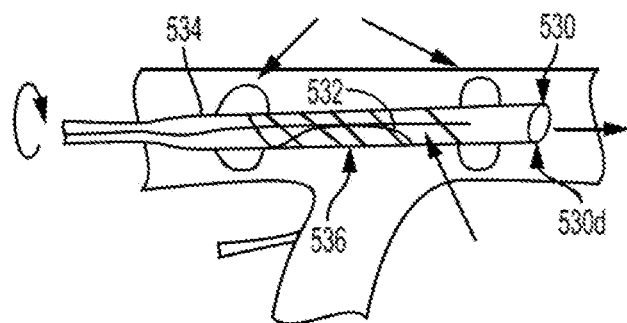
FIG. 23 is a side perspective view of an alternate catheter embodiment having a propeller.

In another embodiment, the catheter can include a propeller disposed in an inner lumen. As shown in FIG. 23, the propeller can be configured to advance fluid from the proximal end of the catheter toward the distal end of the catheter, thereby advancing fluid within the vein of a patient. As discussed above, the catheter can be proximal to the lymphatic duct outflow to create a low pressure zone thereby creating a pressure gradient to allow fluid flow from the lymphatic duct to pass easily into the low pressure zone. For example, the catheter 530 can be configured with a propeller 532 disposed in an inner lumen 534 such that the propeller is configured to rotate axially wherein fluid flows between the first and second restrictions. The propeller can alternatively be actuated by an external force. As fluids flow into the catheter 530 via the suction port 536 the propeller 532 can advance the fluid in a distal direction via the driving force of the propeller 532 to transport the fluid from the distal end 530*d* of the catheter into the innominate vein of the patient. As the fluid is advanced within the vein the low pressure zone is maintained thereby allowing additional fluid to pass from the lymphatic duct into the suction port.

Figure 24:
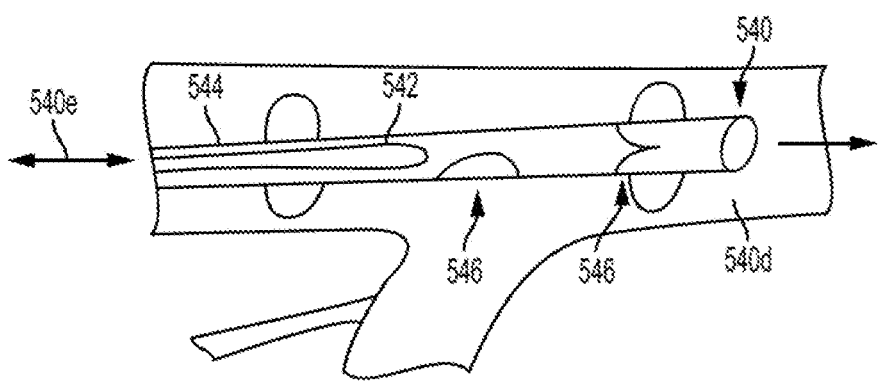
FIG. 24 is a side perspective view of an alternate catheter embodiment having a piston.

As described above, with respect to the catheter configured with a propeller, some catheters can have a self-actuating mechanism to advance the fluid within the catheter. In another embodiment, as shown in FIG. 24, a catheter 540 can be configured with a piston 542 disposed in the inner lumen 544, a suction port that can be positioned toward the midsection of the catheter, a one way valve proximal to the suction port and a one way valve at a distal end of the catheter. The piston can be positioned toward the proximal end of the catheter upstream of a suction port. The piston can be configured to advance and retract axially from the proximal end of the catheter toward the distal end of the catheter. As discussed above, the catheter can be disposed within the vein of a patient proximal to a lymphatic duct. The retraction of the piston toward the proximal end 540*p* of the catheter 500 can create a suction force thereby allowing fluid into the catheter 540 via the suction port 546. The piston 542 is then advanced forward toward the distal end 540*d* of the catheter 500 and can drive fluid forward to discharge the fluid out the distal end 540*d* of the catheter 500 into the vein of the patient. Utilizing this embodiment requires a plurality of one-way valves at the suction port 546 and at the distal end 540*d* of the catheter to prevent fluid back flow.

Figure 25:
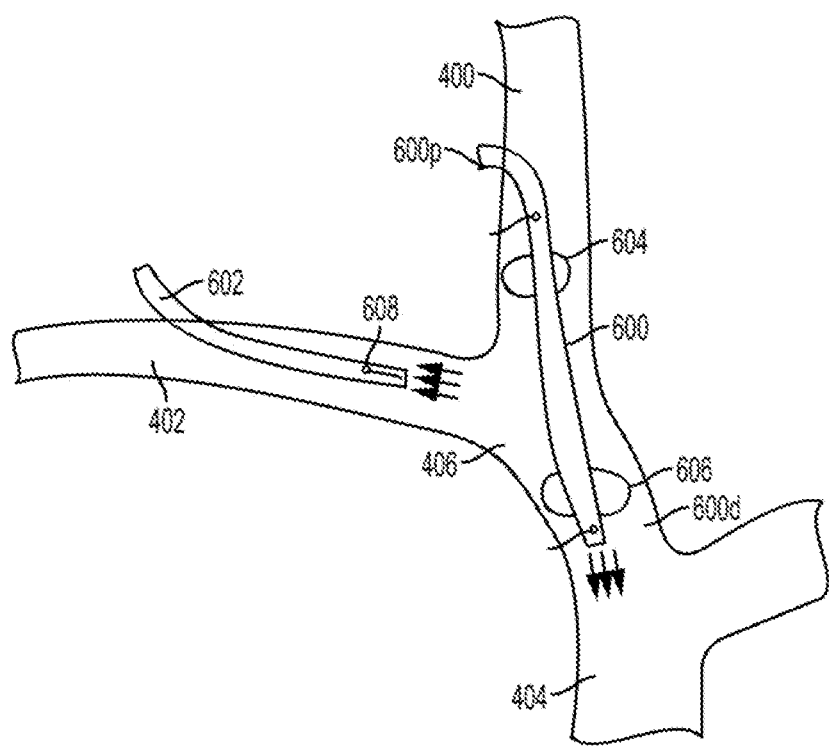
FIG. 25 is a schematic view of an alternate catheter embodiment having a split catheter configuration.

In certain circumstances, a patient's condition or anatomy may not be suitable for treatment using a large venous catheter or an indwelling catheter as described above. In some embodiments, a split action catheter method may be used to reduce the catheter crossing profile. As shown in FIG. 25, a plurality of catheters may be used instead of a single indwelling catheter. For example, a first catheter 600 can include a plurality of lumens including a fluid discharge lumen, a proximal pressure sensor lumen, a distal pressure sensor lumen, a mid-point pressure sensor lumen, a first restriction, a second restriction, and an optional bifurcation pressure lumen. A second catheter 602 can include a fluid suction lumen and an optional bifurcation pressure lumen. The first and the second catheters can be used in conjunction with one another to create a low pressure zone. The first catheter 600 can be inserted into a patient through the internal jugular vein 400 and the second catheter 602 can be inserted into a patient via the subclavian vein 402. After positioning the catheters, the first and second restrictions 604, 606 of catheter 600 can be activated on the first catheter 600 to create a localized low pressure zone proximate to the lymphatic duct. The low pressure zone can facilitate fluid drainage from the lymphatic ducts into the low pressure zone. The fluid can be removed from the low pressure zone via the second catheter 602. As such, fluid can enter the proximal end of the second catheter and pass through the catheter toward its distal end. Outside of the body of the patient, the second catheter can be configured to the first catheter via drainage tubing or the like. The fluid can then travel through the first catheter 600 entering into the proximal end 600$p$ and be discharged via the distal end 600$d$ into the SVC. The pressure gradient can reduce the fluid in the lymphatic system thereby reducing the edema.

Alternate Embodiments

In some embodiments, an alternate activation technique such as mechanical compression can be used to regulate the lymphatic flow. Mechanical compressions can be applied using extra body elements or with implantable elements that are preferably implanted in the torso. For example, mechanical compression elements can change their volumes on demand and thereby enhance the lymphatic flow. In some embodiments, a balloon can be implanted in the thoracic cavity proximate to the alveoli. At elevated pressures, the balloon can inflate and the pressures around the entrance to the lymphatic vessels can be increased. The pressure gradient can facilitate fluid flow into the lymphatic system. In some embodiments, lymphatic flow can be regulated used muscle activation. For example, the diaphragm muscle can be utilized to control the pressure in the torso and the lungs and can be synchronized to patient breathing patterns. Alternatively, the lymphatic muscles can be contracted to increase the rate and strength of contraction of the intrinsic or extrinsic pumps. The contraction pacing can enhance the natural pumping actions thereby enhancing lymphatic return.

Figure 18:
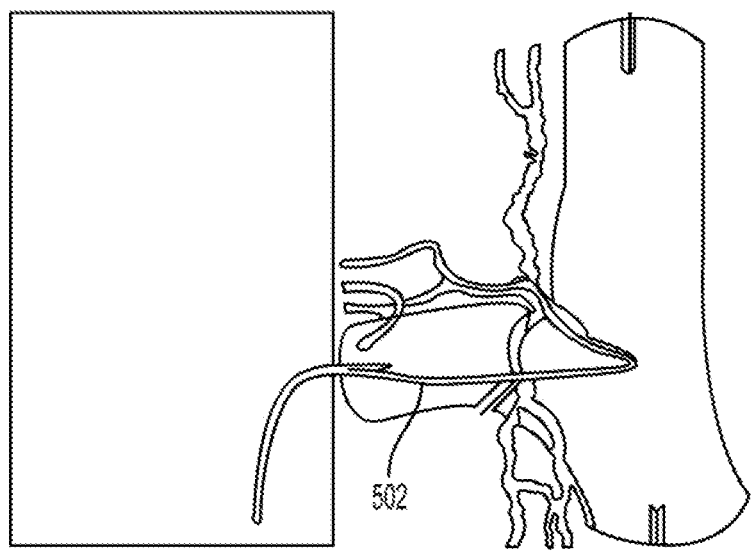
FIG. 18 is a schematic view of an alternate activation technique including electrical stimulation.

In other embodiments, an alternate activation technique such as electrical simulation can be used to increase the lymphatic flow. As shown in FIG. 18, a wire 502 with electrical stimulation electrodes can be placed using catheterization in the thoracic duct and or the lymphatic duct vessels. The electrical stimulation can generate peristaltic action in the thoracic duct and/or the lymphatic duct vessels. In another embodiment, electrodes or an array of electrodes can be placed in the trachea. The electrode can be proximate to the lymphatic vessels and will generate stimulation that can increase the lymphatic flow.

Figure 26:
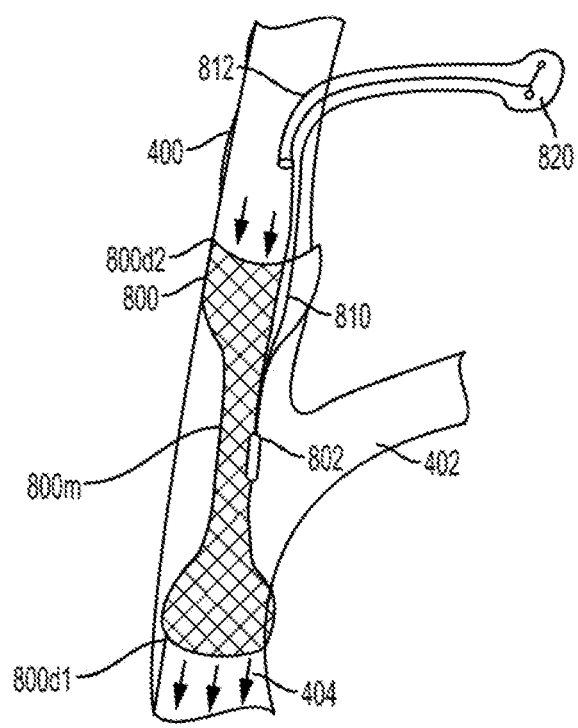
FIG. 26 is a schematic view of an alternate catheter embodiment having a configuration with dual tapered ends.

In another embodiment, shown in FIG. 26, a covered stent 800 with two tapered ends 800$d$1, 800$d$2 can be implanted in the jugular vein 400 in proximity to the innominate vein 404. The large diameter ends 800$d$1, 800$d$2 of the covered stent 800 are in contact with the entire vessel circumference. As shown, the thinner neck section 800$m$ of the stent 800 is positioned near the subclavian vein ostium 402 or the venous angle. The entire flow of blood coming from the jugular vein 400 is directed into the covered stent 800 and reaches the innominate vein 404. The covered stent 800 has an opening 802 in the neck section 800$m$ that is connected to a suction tube 810 that can be connected, for example, to an extracorporeal pump 820, such as a peristaltic pump. This configuration enables the suction of blood from the subclavian vein and the lymphatic duct and thus creates a low pressure zone between the two tapered ends 800$d$1, 800$d$2 of the stent 800. The blood can be returned to the jugular vein 400 via a discharge tube 812. The volume of blood that is circulated via the pump is lower because the natural blood flow coming from the jugular vein is directed into the innominate vein and does not circulated through the pump.

Figure 27:
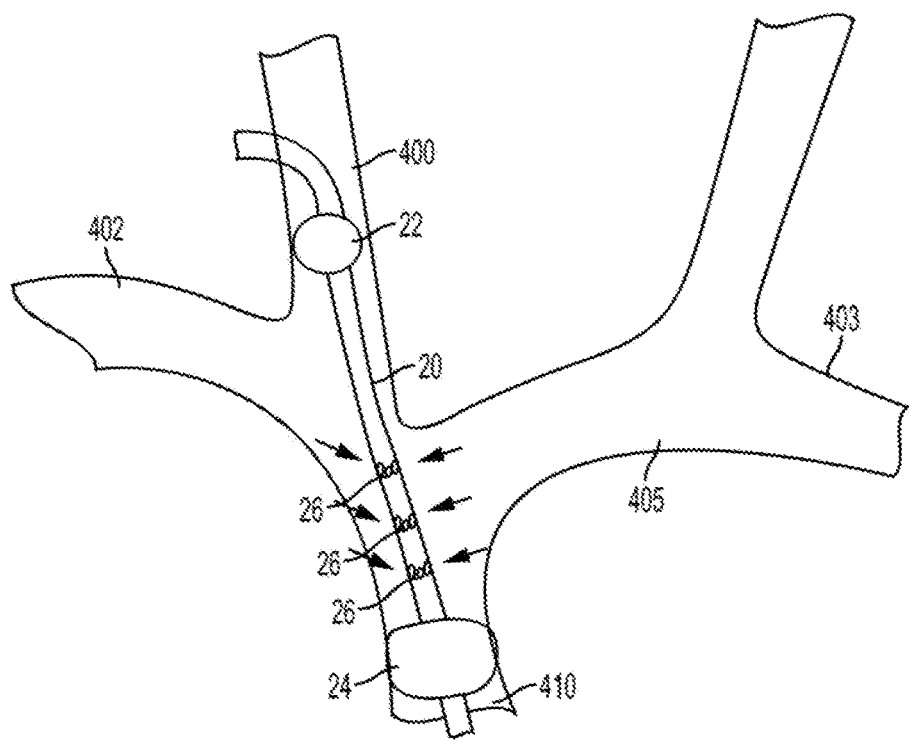
FIG. 27 is a schematic view of an alternative embodiment in which the catheter is positioned in both the jugular vein and the superior vena cava.

In another embodiment, shown in FIG. 27, the catheter 20 can be positioned such that the distal restriction 24 is positioned within the superior vena cava (SVC) 410 and the proximal restriction is within the right internal jugular vein 400. The positioning of the suction port(s) 26 between the proximal and distal restrictions is such that blood can be withdrawn from the right subclavian vein 402, and from the left innominate vein 403. This arrangement enables drainage of both the right lymphatic duct and the thoracic duct.

Figure 28:
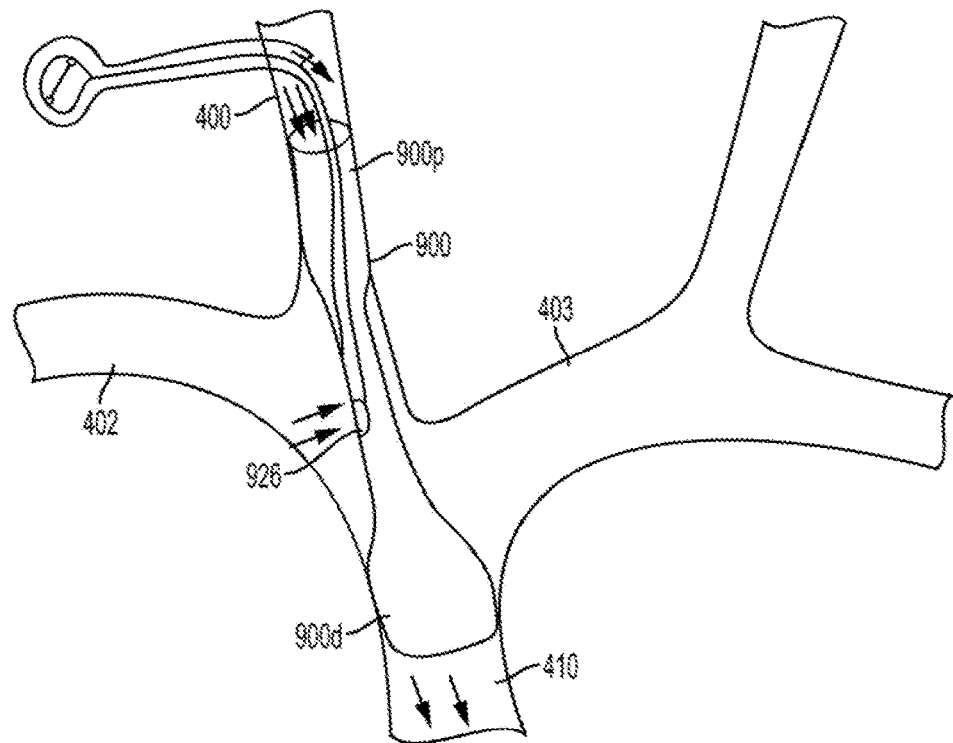
FIG. 28 is a schematic view of an alternate catheter embodiment having a configuration with dual tapered ends positioned in both the jugular vein and the superior vena cava.

In a further embodiment, shown in FIG. 28, a covered stent 900 with tapered end sections is inserted into the right internal jugular vein 400 such that the proximal portion 900$p$ remains positioned within the jugular vein and the distal portion 900$d$ is positioned within the SVC 410. The suction port 926 in the neck region 900$n$ enables suction of blood from the right subclavian vein 402, and from the innominate vein 403. Such arrangement enables drainage of both the right lymphatic duct and the thoracic duct.

Figure 29:
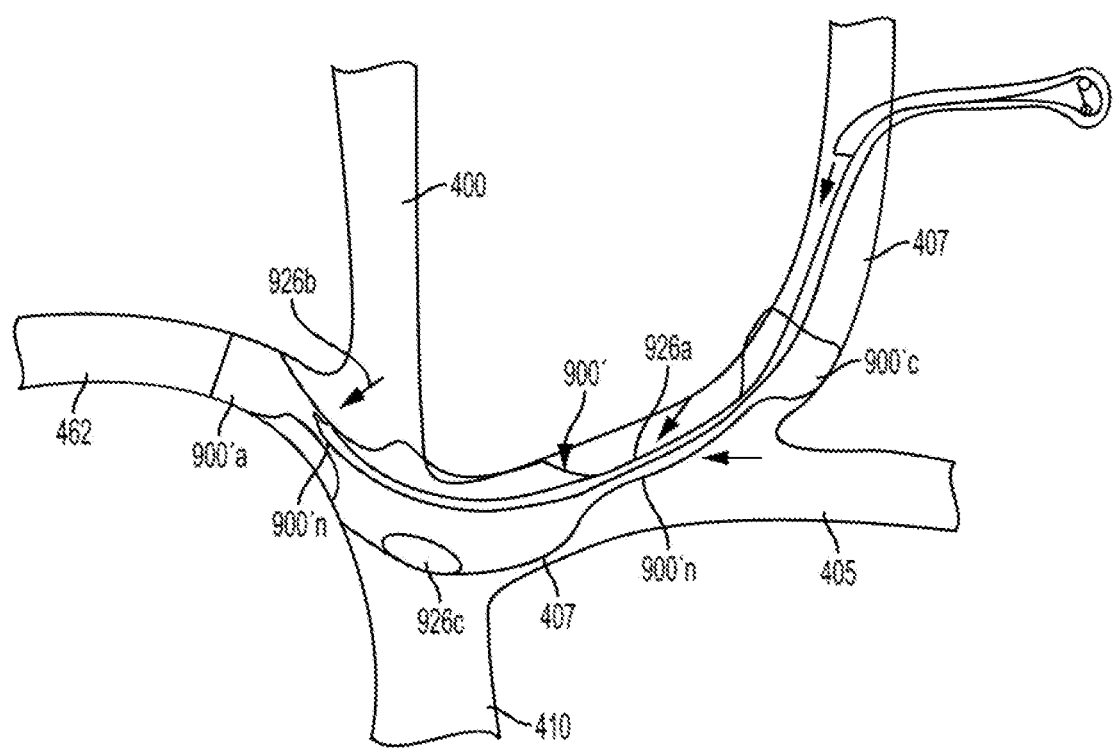
FIG. 29 is a schematic view of an alternate catheter embodiment having three tapered sections.

FIG. 29 illustrates another embodiment in which the a covered stent 900' with three tapered sections 900'$a$, 900'$b$, 900'$c$ is inserted via the left internal jugular vein 407 into the right subclavian vein 402. The covered stent 900' is covered between its two opposite ends with two openings 926$a$, 926$b$ which are located in each of the neck sections 900'$n$ and another larger opening 926$c$, which is located in the middle, larger diameter section 900$b$ and oriented toward the SVC 410. The blood flowing through the left internal jugular vein and right subclavian vein is directed into the SVC. The right jugular vein flow and left subclavian vein flow are suctioned through the catheter together with flow from both lymphatic vessels, and is return to the vasculature proximally of the stent into the superior section of the left internal jugular vein. In such an embodiment the stent 900' can be placed from either side (subclavian or jugular vein) to either opposite vessel. For example, the stent 900' can extend between the left jugular vein 407 and right jugular vein 400, or between right jugular vein 400 and the left subclavian vein 405. A variety of other positioning combinations are also possible, depending upon a patient's anatomy, as will be understood by a person skilled in the art.

Figure 30:
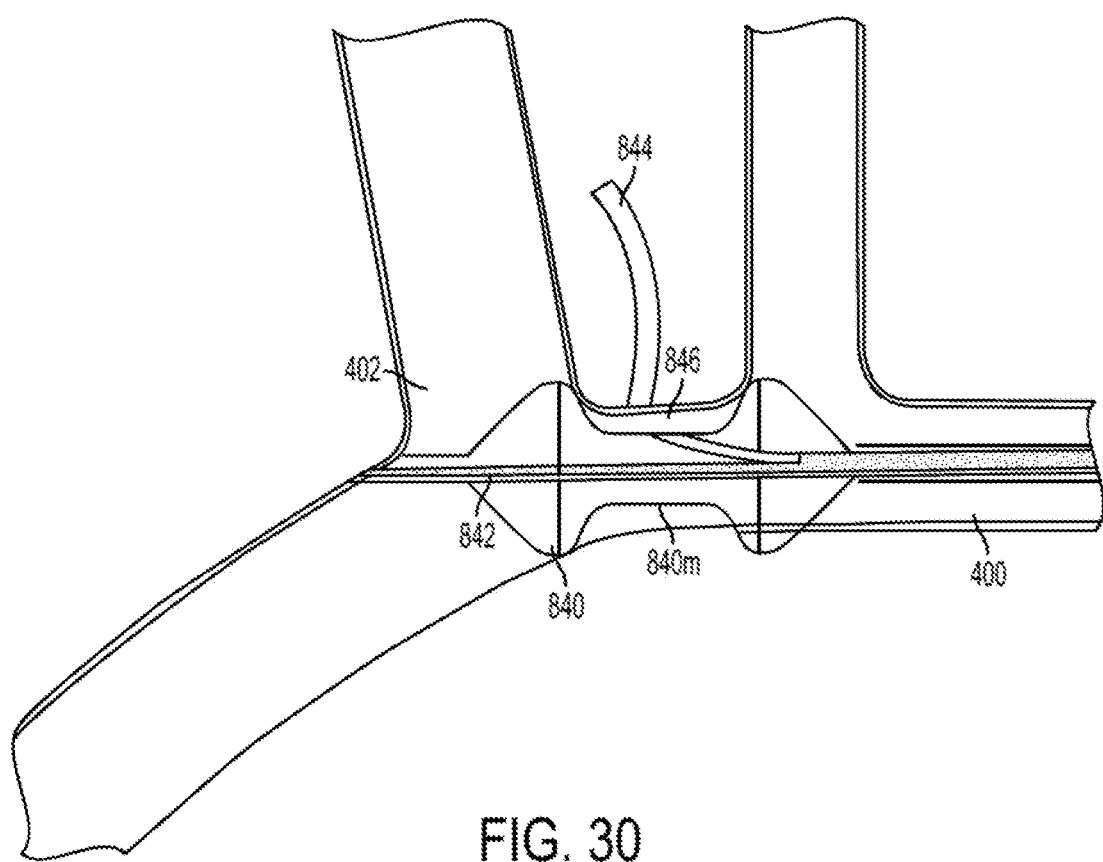
FIG. 30 is a schematic view of an alternate catheter embodiment having an hourglass configuration.

In another embodiment, shown in FIG. 30, a stent 840 having a somewhat hour glass shape, can be implanted within the left jugular vein 400 in proximity to the subclavian vein 402. As shown, a thinner, central region 840$m$ of the stent is positioned distal to the subclavian vein 402 and in proximity to the lymphatic duct entry. The stent 840 includes a lumen 842 extending therethrough to accommodate blood flow and a suction tube 844 having a suction port 846 formed in the thinner, central region 840$m$ of the stent 840. The suction port 846 and suction tube 844 are in fluid communication with an external pump (not shown). In use, the entire blood volume is directed into and through the stent and the pump is required to circulate only the lymphatic fluid that is withdrawn through the suction tube and the suction port.

Figure 19:
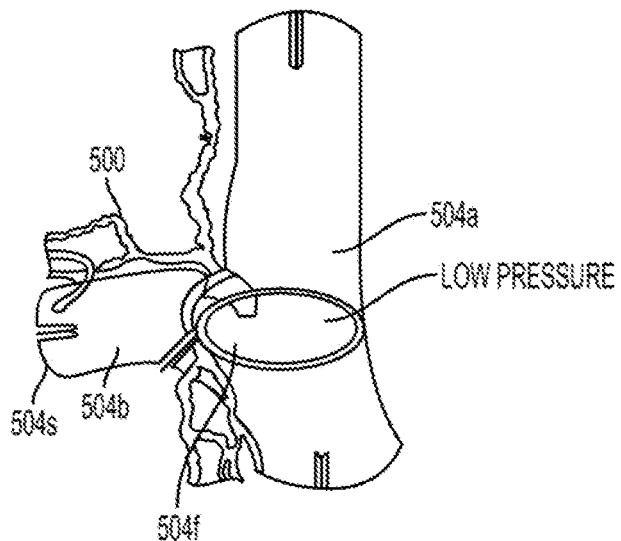
FIG. 19 is a schematic view of an alternate pressure gradient creation method including a plurality of restrictor stents positioned proximate to a lymphatic duct.

In an alternate embodiment, one or more restriction stents can be implanted to create a low pressure region proximate to the lymphatic duct. As shown in FIG. 19, conical stents 504a, 504b can be implanted at the outflow junction of the lymphatic duct with the subclavian or jugular vein. The stents 504a, 504b can have a first end 504f with a first diameter and a second end 504s with a diameter larger than the first diameter. The first end 504f can be position in the lymphatic junction thereby creating a lower pressure gradient in the vein proximate to the first end 504f of the stent than the regulating central venous pressure. Placement of the stent can create a pressure gradient along the lymphatic vessels thereby facilitating drainage from the lymphatic vessels. Applying the Bernoulli equation that conserves energy if the cross section of the flow is reduced, the speed of the flow is increased (A1V1=A2V2). In this embodiment, when the velocity of the fluid increases, due to the Bernoulli equation, the pressure must drop.

Figure 20:
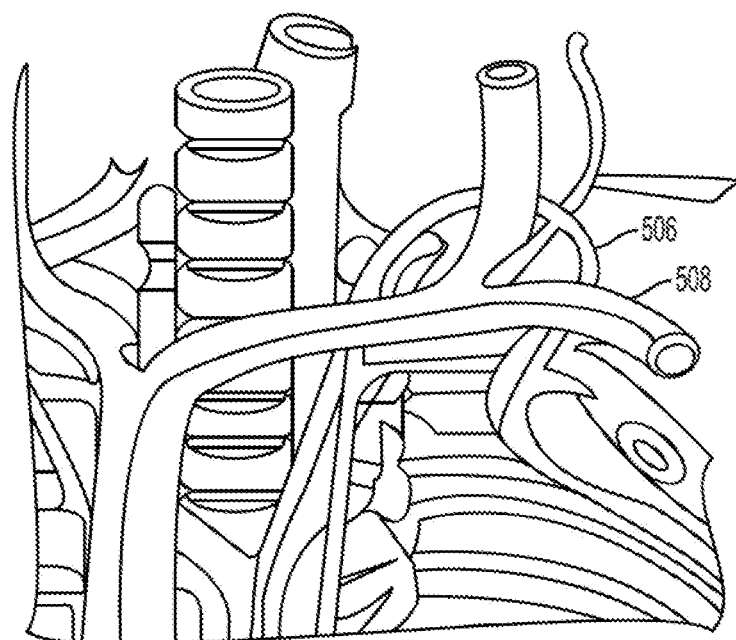
FIG. 20 is a schematic view of an alternate method of fluid path creation depicting a kink resistant stent placed within a thoracic duct of a patient.

In some embodiments, a kink resistant stent 506 can be implanted in the thoracic duct 508 at the location where the duct makes a 180 degree turn. The fluid flow can be restricted or impleaded by an obstruction or kink thereby impeding fluid clearance. As shown in FIG. 20, placement of the stent can facilitate fluid clearance by maintaining an open passage, thereby enhancing flow back into the venous circulation. In some embodiments, the stent may include a one way valve to prevent backflow of the fluid.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for draining lymph fluid from a thoracic duct of a subject, the system comprising:
    an interventional device configured to fluidically communicate with a thoracic duct of the subject, the interventional device comprising one or more openings to receive a fluid from the thoracic duct of the subject; and
    a drainage channel coupled to the interventional device at a first end and having a length such that when the interventional device is in fluid communication with the thoracic duct of the subject, a second end of the drainage channel extends external the subject such that a pressure gradient between the one or more openings of the interventional device and the second end of the drainage channel causes fluid from the thoracic duct to enter the interventional device and flow through the drainage channel to the second end, wherein the interventional device removes fluid from the thoracic duct without restricting fluid flow downstream of the thoracic duct.

2. The system of claim 1, wherein the system is configured to withdraw only lymphatic fluid from the subject.

3. The system of claim 2, wherein the one or more openings comprise suction ports.

4. The system of claim 3, wherein the withdrawal of only lymphatic fluid comprises suction of lymphatic fluid through at least one suction port.

5. The system of claim 1, wherein the interventional device comprises a catheter and the one or more openings are one or more suction ports in the catheter.

6. The system of claim 5, wherein the catheter is configured to create a suction force allowing fluid into the catheter via the one or more suction ports.

7. The system of claim 1, wherein the interventional device is configured to create a low-pressure area such that lymph fluid is drained into the low-pressure area.

8. The system of claim 1, wherein the interventional device comprises an indwelling portion that is configured for advancement in the subject.

9. The system of claim 1, wherein the interventional device is configured to maintain a pressure gradient.

10. The system of claim 1, wherein the system further comprises a pump and a hemofilter operably associated with the drainage channel and configured to remove an additional volume of fluid from the subject.

11. The system of claim 1, wherein the second end is configured for placement outside the body of the subject.

12. The system of claim 1, wherein the drainage channel comprises a length that allows for percutaneous insertion of the interventional device in the subject while the second end of the drainage channel extends external the subject.

13. The system of claim 12, wherein the length is 15 cm.

14. The system of claim 1, wherein, during operation, the system facilitates blood flow through a blood vessel concurrent with fluid flowing from the thoracic duct into the interventional device inside the blood vessel.

15. The system of claim 1, wherein the interventional device is configured to receive fluid from the thoracic duct without blocking blood flow around the thoracic duct.

* * * * *